US006454811B1

(12) United States Patent
Sherwood et al.

(10) Patent No.: US 6,454,811 B1
(45) Date of Patent: Sep. 24, 2002

(54) COMPOSITES FOR TISSUE REGENERATION AND METHODS OF MANUFACTURE THEREOF

(75) Inventors: Jill K. Sherwood, Princeton, NJ (US); Linda G. Griffith, Cambridge, MA (US); Scott Brown, Princeton, NJ (US)

(73) Assignees: Massachusetts Institute of Technology, Cambridge, MA (US); Therics, Inc., Princeton, NJ (US)

( * ) Notice: Subject to any disclaimer, the term of this patent is extended or adjusted under 35 U.S.C. 154(b) by 0 days.

(21) Appl. No.: 09/416,346

(22) Filed: Oct. 12, 1999

Related U.S. Application Data
(60) Provisional application No. 60/103,853, filed on Oct. 12, 1998.

(51) Int. Cl.[7] .................................................. A61P 2/02
(52) U.S. Cl. ................................. 623/23.76; 623/23.72
(58) Field of Search ................................. 623/23.76, 17

(56) References Cited

U.S. PATENT DOCUMENTS

| | | |
|---|---|---|
| 4,060,081 A | 11/1977 | Yannas et al. |
| 4,485,097 A | 11/1984 | Bell |
| 4,520,821 A | 6/1985 | Schmidt et al. |
| 4,609,551 A | 9/1986 | Caplan et al. |
| 4,620,327 A | 11/1986 | Caplan et al. |
| 4,787,900 A | 11/1988 | Yannas |
| 4,846,838 A | 7/1989 | Takai et al. |
| 4,927,632 A | 5/1990 | Wong |

(List continued on next page.)

FOREIGN PATENT DOCUMENTS

| | | |
|---|---|---|
| DE | 41 02 259 A1 | 7/1992 |
| WO | WO93/08850 A1 | 5/1993 |
| WO | WO 95/11007 A1 | 4/1995 |
| WO | WO 96/40002 A1 | 12/1996 |
| WO | WO 98/36739 A1 | 8/1998 |
| WO | WO 98/41189 A1 | 9/1998 |

OTHER PUBLICATIONS

Boeree, et al., "Development of a degradable composite for orthopedic use: mechanical evaluation of an hydroxyapatite–polyhydroxybutyrate composite material," *Biomaterials* 14:793–96 (1993).

Bresina, "The Treatment of Bone Defects," *Proceedings of the Fourth World Biomaterials Congress*, Berlin, Federal Republic of Germany, p 207, Apr. 1992.

(List continued on next page.)

*Primary Examiner*—Corrine McDermott
*Assistant Examiner*—Alvin Stewart
(74) *Attorney, Agent, or Firm*—Holland & Knight LLP

(57) ABSTRACT

Composite devices for tissue engineering are provided having a gradient of one or more of the following: materials, macroarchitecture, microarchitecture, or mechanical properties, which can be used to select or promote attachment of specific cell types on and in the devices prior to and/or after implantation. In various embodiments, the gradient forms a transition zone in the device from a region composed of materials or having properties best suited for one type of tissue to a region composed of materials or having properties suited for a different type of tissue. The devices are made in a continuous process that imparts structural integrity as well as a unique gradient of materials in the architecture. The gradient may relate to the materials, the macroarchitecture, the microarchitecture, the mechanical properties of the device, or several of these together. The devices disclosed herein typically are made using solid free form processes, especially three-dimensional printing process (3DP™). The device can be manufactured in a single continuous process such that the transition from one form of tissue regeneration scaffold and the other form of tissue regeneration scaffold have no "seams" and are not subject to differential swelling along an axis once the device is implanted into physiological fluid.

62 Claims, 4 Drawing Sheets

U.S. PATENT DOCUMENTS

| | | | |
|---|---|---|---|
| 4,985,036 A | | 1/1991 | Lommen et al. |
| 5,011,692 A | | 4/1991 | Fujioka et al. |
| 5,059,123 A | | 10/1991 | Jernberg |
| 5,108,926 A | | 4/1992 | Klebe |
| 5,171,261 A | | 12/1992 | Noishiki et al. |
| 5,197,985 A | | 3/1993 | Caplan et al. |
| 5,204,055 A | * | 4/1993 | Sachs et al. ............... 419/2 |
| 5,226,914 A | | 7/1993 | Caplan et al. |
| 5,260,009 A | | 11/1993 | Penn |
| 5,270,300 A | | 12/1993 | Hunziker |
| 5,338,772 A | | 8/1994 | Bauer et al. |
| 5,348,788 A | | 9/1994 | White |
| 5,370,692 A | | 12/1994 | Fink et al. |
| 5,387,380 A | | 2/1995 | Cima et al. |
| 5,447,724 A | | 9/1995 | Helmus et al. |
| 5,460,758 A | * | 10/1995 | Langer et al. ............ 264/401 |
| 5,466,462 A | | 11/1995 | Rosenthal et al. |
| 5,490,962 A | | 2/1996 | Cima et al. |
| 5,496,372 A | | 3/1996 | Hamamoto et al. |
| 5,510,066 A | | 4/1996 | Fink et al. |
| 5,514,378 A | | 5/1996 | Mikos et al. |
| 5,518,680 A | | 5/1996 | Cima et al. |
| 5,607,474 A | | 3/1997 | Athanasiou et al. |
| 5,626,861 A | | 5/1997 | Laurencin et al. |
| 5,681,572 A | | 10/1997 | Seare, Jr. |
| 5,869,170 A | | 2/1999 | Cima et al. |
| 5,876,452 A | * | 3/1999 | Athanasiou et al. .......... 623/16 |
| 6,176,874 B1 | * | 1/2001 | Vacanti et al. ............ 623/1.44 |
| 6,197,575 B1 | * | 3/2001 | Griffith et al. ........... 435/288.4 |
| 6,224,630 B1 | * | 5/2001 | Bao et al. ................. 623/17 |
| 6,258,870 B1 | * | 7/2001 | Hubbell et al. ............. 522/26 |
| 6,261,493 B1 | * | 7/2001 | Gaylo et al. ............... 264/86 |
| 6,270,335 B2 | * | 8/2001 | Leyden et al. ............ 425/375 |

OTHER PUBLICATIONS

Burns, "Introduction to Desktop Manufacturing and Prototyping," *Rapid Prototyping: System Selection and Implementation Guide*, pp 2–9, 1992.

Chow, "Calcium Phosphate Materials: Reactor Response," *Adv. Dent. Res.* 2(1):181–86 (1988).

Cima & Sachs, "Three Dimensional Printing: Form, Materials, and Performance," *Quarterly Report 1991, Proceedings of the Solid Free–form Fabrication Symposium,* University of Texas, pp. 187–194, 1991.

Cima, et al., "Tissue Engineering by Cell Transplantation Using Degradable Polymer Substrates," *J. Biomechan. Eng.* 113:143–51 (1991).

Damien & Parsons, "Bone Graft and Bone Graft Substitutes: A Review of Current Technology and Applications," *J. Appl. Biomater.* 2:187–208 (1991).

De Groot, "Effect of Porosity and Physiochemical Properties on the Stability, Resorption, and Strength of Calcium Phosphate Ceramics," *Annals New York Academy of Sciences* 523:227–33 (1988).

De Groot, et al., "Significance of the Porosity and Physical Chemistry of Calcium Phosphate Ceramics:Dental and other Head and Neck Uses," *Annals New York Academy of Sciences* 523:272–75 (1988).

Dennis, et al., "Osteogenesis in marrow–derived mesenchymal cell porous ceramic composites transplanted subcutaneously: effect of fibronectin and laminin on cell retention and rate of osteogenic expression," *Cell Transplant.* 1(1):23–32 (1992).

Erbe, et al., "Geometrically surface Structured Stereolithography Acrylic Resin and Titanium Implants," *Proceedings of the Fourth World Biomaterials Congress,* Berlin, Federal Republic of Germany, p 165, 1992.

Hulbert, et al., "Potential of ceramic materials as permanently implantable skeletal prostheses," *J. Biomed. Mater. Res.* 4(3):433–56 (1970).

Kaplan, "3–D CT Images for Facial Implant Design and Manufacture," *Clinics in Plastic Surgery* 14(4):663–76 (1987).

Koren, et al., "Characterization of a monoclonal antibody that binds equally to all apolipoprotein forms of human plasma apolipoprotein B. I. Specificity and binding studies," *Biochimica et Biophysica Acta* 876:91–100 (1986).

Lakshminarayan & Marcus, "Microstructural an Mechanical Properties of $AI_2O_3/P_2O_5$ and $AI_2O_3/B_2O$ Composites Fabricated by Selective Laser Sintering," *Proceedings of the Solid Freeform Fabrication Symposium, University of Texas,* pp. 205–212, 1991.

Lee, et al., "Protein–resistant surfaces prepared by PEO- –containing block copolymer surfactants," *J. Biomed. Mat. Res.* 23:351–68 (1989).

Legeros, "Calcium Phosphate Materials in Restorative Dentistry: A Review," *Adv. Dent. Res.* 2(1):164–80 (1988).

Legeros, et al., "Significance of the Porosity and Physical Chemistry of Calcium Phosphate Ceramics Biodegradation –Bioresorption," *Annals New York Academy of Sciences* 523:268–71 (1988).

Lemons, et al., "Significance of the Porosity and Physical Chemistry of Calcium Phosphate Ceramics," *Annals New York Academy of Sciences* 523:278–82 (1988).

Martin, et al., "Bone ingrowth and mechanical properties of coralline hydroxyapatite 1 yr after implantation," *Biomaterials* 14(5):341–48 (1993).

Milthorpe, "Three Dimensional Reconstruction of Biomaterial Histological Images," *Proceedings of the Fourth World Biomaterials Congress,* p. 564, Berlin, Federal Republic of Germany, 1992.

Piecuch, "Extraskeletal implantation of a porous hydroxyapatite ceramic," *J. Dent. Res.* 61(12):1458–60 (1982).

Sachs, et al., "CAD–Casting: Direct Fabrication of Ceramic Shells and Cores by Three Dimensional Printing" *Manufacturing Review* 5(2):117–26 (1992).

Vacanti, et al., "Beyond Transplantation," *Arch. Surg.* 123:545–49 (1988).

Vacanti, et al., "Selective Cell Transplantation Using Bio-absorbable Artificial Polymers as Matrices," *J. Pediatric Surgery.* 23:3–9 (1988).

\* cited by examiner

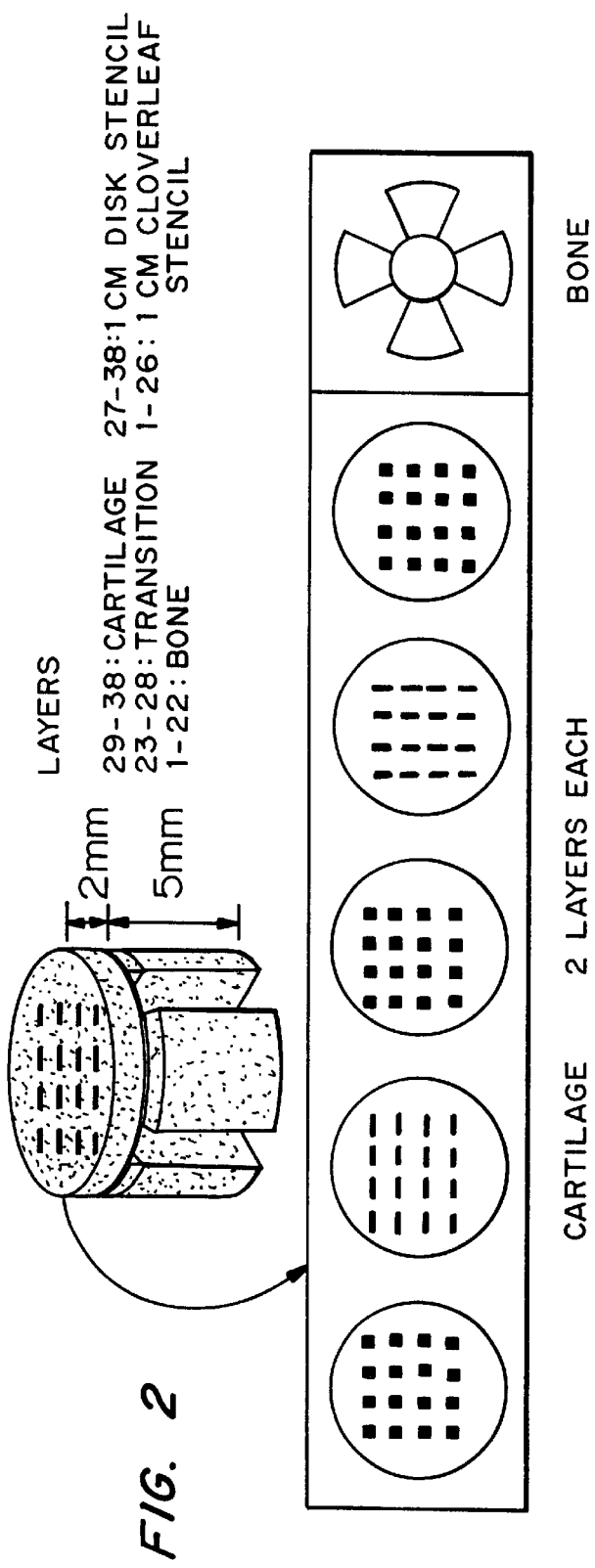
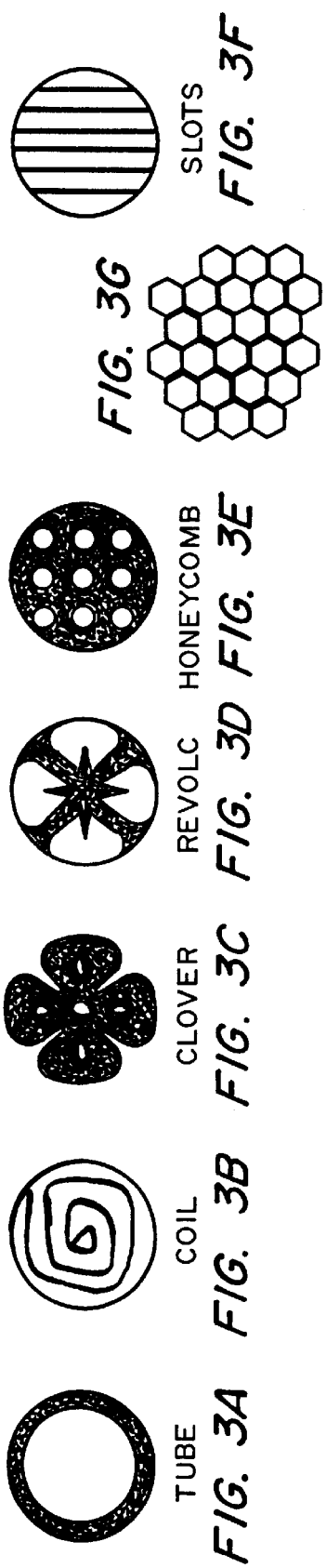

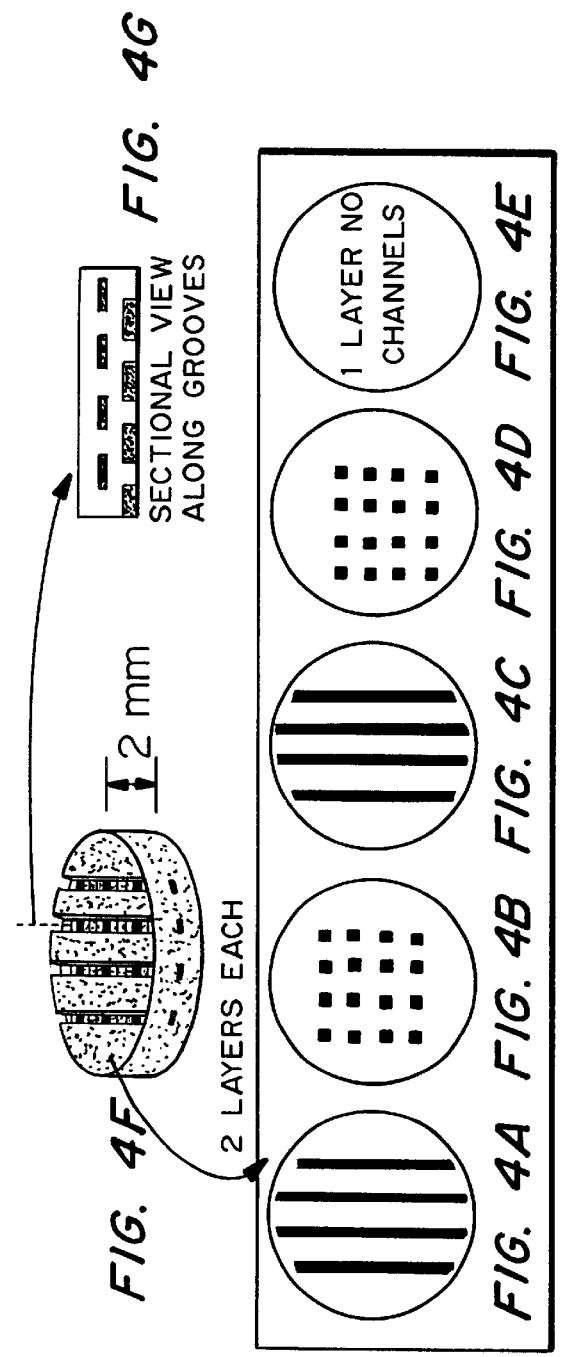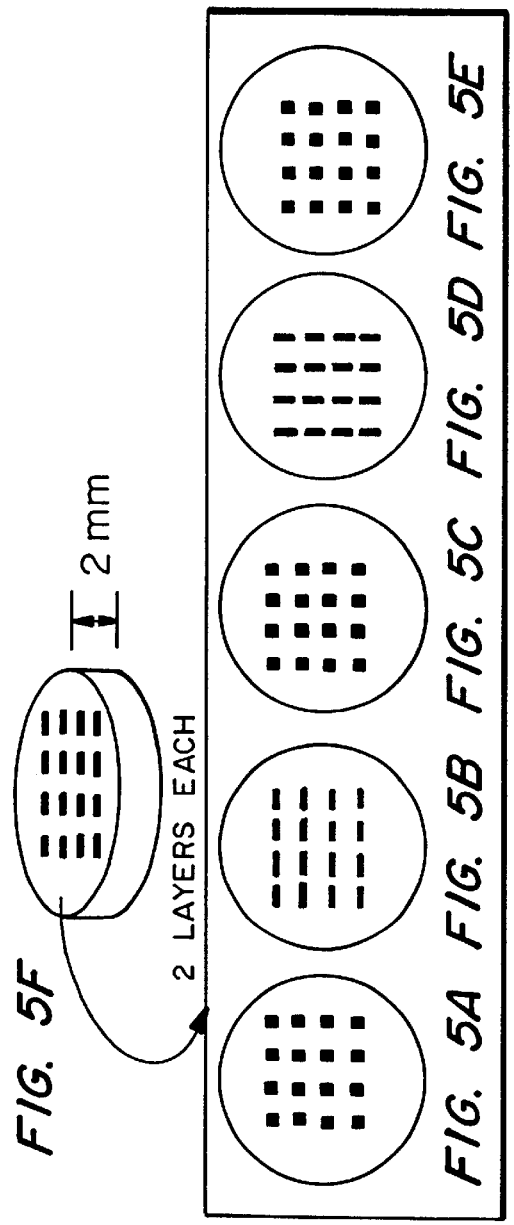

COMPOSITES FOR TISSUE REGENERATION AND METHODS OF MANUFACTURE THEREOF

CROSS-REFERENCE TO RELATED APPLICATIONS

Priority is claimed to U.S. provisional application Serial No. 60/103,853, filed Oct. 12, 1998.

FIELD OF THE INVENTION

The invention relates generally to implantable devices characterized by gradients of materials, architecture, and/or properties for tissue regeneration, made using solid free-form fabrication technology, which can be combined with computer-aided design.

BACKGROUND OF THE INVENTION

Bone deficit or defects may result from congenital defects, disease, aging, or trauma. Bones are composed of highly vascularized tissue, called osseous tissue, which harbors blood-forming elements, the marrow. The external and internal structure of bone is in dynamic flux: the cellular elements produce and remodel a matrix of cartilage in which calcium salts are deposited. Approximately two-thirds of mature bone is calcium phosphate as hydroxyapatite, one third is predominantly collagen fibers and other calcium salts, while only 2% by weight is living cells. Through processes of calcium resorption and deposition, osteocytes and various other cell types are able to remodel or heal bone as needed while the skeleton continues to provide structural support for the body.

Bone is further divided into dense (compact) and spongy (cancellous) areas. Because it has the greater mechanical strength, compact bone is positioned to receive the greatest physical loads generated by the weight of the body and skeletal muscle contractions. Compact bone forms along the surface of the long axis of the long bones forming what is known as the cortex of the bone. Spongy bone composes the "head" (epiphysis) and the inner areas of the bones, and borders the medullary cavity in the larger bones.

Cartilage, on the other hand, is an avascular tissue composed of 5–10% by weight of living cells. There are three major types of cartilage in the body: hyaline, fibrocartilage, and elastic cartilage. Hyaline cartilage covers the epiphyses of the bone and, in synovial joints, lies within a fluid filled capsule. Fibrocartilage composes the intervertebral discs separating the vertebrae of the spinal columns. Elastic cartilage is present in areas requiring extreme resilience, such as the tip of the nose. Cartilage is formed by and contains cells called chondrocytes. The extracellular matrix of hyaline cartilage contains closely packed Type II collagen fibers and proteoglycans including hyaluronate and glycoaminoglycans in a chondroitin sulfate matrix. Chondrocytes receive nutrients and dispose of wastes by diffusion through the matrix and are believed to have limited mobility or ability to divide and regenerate damaged tissue. Chondrocytes normally produce anti-angiogenesis factors. However, when large areas of cartilage are damaged, overgrowth by fibroblasts and neovascularization of the area may result in the formation of scar tissue or callus instead of articular cartilage. A subsequent ingrowth of bone forming cells may result in calcium deposition in these areas, causing further deformation of the local area.

The interface between bone and cartilage is therefore the interface between a vascularized and avascular tissue as well as mineralized (ossified) and nonminerilized collagen matrices. Traumatic injury, as well as such conditions as osteoarthritis and aging, often result in damage to the articular cartilage, which may also involve damage to the underlying bone. Therefore, there is a need for a method of treatment which meets the disparate needs of both tissue types and allows or encourages the healing process to progress towards restoration of both types of tissues at the same site.

Clinical use of grafts of living tissue have recently moved from direct implantation of freshly harvested fully formed tissue, e.g. skin grafts or organ transplants, to strategies involving seeding of cells on matrices which will regenerate or encourage the regeneration of local structures. For complex and weight bearing hard tissues, there is an additional need to provide mechanical support of the existing structure by replacement or substitution of the hard tissue for at least some of the healing period. Thus, the device must serve as a scaffold of specific architecture which will encourage the migration, residence and proliferation of specific cell types as well as provide mechanical and structural support during healing. In the case of devices for regeneration of articular (hyaline) cartilage, it is important that the device be completely resorbable, as residual material may compromise the surface integrity (smoothness) and overall strength and resilience of the regenerated tissue.

In order to encourage cellular attachment and growth, the overall porosity of the device is important. Additionally, the individual pore diameter or size is an important factor in determining the ability of cells to migrate into, colonize, and differentiate while in the device (Martin, R B et al. *Biomaterials*, 14: 341, 1993). For skeletal tissues, bone and cartilage, guided support to reproduce the correct geometry and shape of the tissue is thought to be important. It is generally agreed that pore sizes of above 150 $\mu$m and preferably larger (Hulbert, et al., 1970; Klawitter, J. J, 1970; Piecuch, 1982; and Dennis, et al., 1992) and porosity greater than 50% are necessary for cell invasion of the carrier by bone forming cells. It has been further accepted that a tissue regenerating scaffold must be highly porous, greater than 50% and more preferably more than 90%, in order to facilitate cartilage formation.

It is well documented that the physiological processes of wound healing and tissue regeneration proceed sequentially with multiple cell types and that cellular factors play a role. For example, thrombi are formed and removed by blood elements, which are components of cascades regulating both coagulation and clot lysis. Cells which are not terminally differentiated, such as fibroblasts, migrate into the thrombus and lay down collagen fibers. Angiogenic cells are recruited by chemotactic factors, derived from circulating precursors or released from cells, to form vascular tissue. Finally, cells differentiate to form specialized tissue. The concept of adding exogenous natural or synthetic factors in order to hasten the healing process is also an area of intense exploration, and numerous growth factors, such as cytokines, angiogenic factors, and transforming factors, have been isolated, purified, sequenced, and cloned. Determining the correct sequence and concentration in which to release one or multiple factors is another area of research in the field of tissue engineering.

Several attempts to address some of the above problems of tissue regeneration in a graft or implantable device have been disclosed. U.S. Pat. No. 5,270,300 describes a method for treating defects or lesions in cartilage or bone which provides a matrix, possibly composed of collagen, with pores large enough to allow cell population, and which further contains growth factors or other factors (e.g. angiogenesis factors) appropriate for the type of tissue desired to be regenerated. U.S. Pat. No. 5,270,300 specifically teaches the use of TGF-beta in the matrix solution as a proliferation and chemotactic agent at a lower concentration and at a subsequent release of the same factor at a higher concentration to induce differentiation of cartilage repair cells. In the case of a defect in adjoining bone and cartilage, a membrane is secured between the bone-regenerating matrix and the cartilage-regenerating matrix to prevent blood vessel penetration from one site to the other site.

U.S. Pat. No. 5,607,474 to Athanasiou et al. describes a molded carrier device comprising two bioerodible polymeric materials having dissimilar mechanical properties arranged proximate to each other for the purpose of being placed in the body adjoining two dissimilar types of tissues. Each polymeric material has a variable degree of porosity or pore sizes into which tissue cells can enter and adhere. The two components of the device are fabricated separately and, e.g., bonded together in a mold. Other features, such as larger passages for cell access, can be mechanically placed in the device.

U.S. Pat. No. 5,514,378 attempts to address some of the requirements of providing a highly porous biocompatible and bioerodible device using a method of forming membranes from a polymer and particle solution. The pores are created by removing the particles, achieved by dissolving and leaching them away in a solvent, such as water, which does not dissolve the polymer, thereby leaving a porous membrane. The polymer must be soluble in a non-aqueous solvent and is limited to synthetic polymers. Once the membrane is created it may be cast into the desired shape. It is envisioned that such membranes could also be laminated together to form a three-dimensional shape.

It has been further recognized that not only the morphology of such devices but the materials of which they are composed will contribute to the regeneration processes as well as the mechanical strength of the device. For example, some materials are osteogenic and stimulate the growth of bone forming cells; some materials are osteoconductive, encouraging bone-forming cell migration and incorporation; and some are osteoinductive, inducing the differentiation of mesenchymal stem cells into osteoblasts. Materials which have been found to be osteogenic usually contain a natural or synthetic source of calcium phosphate. Osteoinductive materials include molecules derived from members of the transforming growth factor-beta (TGF-beta) gene superfamily including: bone morphogenetic proteins (BMPs) and insulin-like growth factors (IGFs).

U.S. Pat. No. 5,626,861 teaches a composite material for use as bone graft or implant composed of biodegradable, biocompatible polymer and a particulate calcium phosphate, hydroxyapatite. The calcium phosphate ceramic was added in order to increase the mechanical strength over the polymer alone and to provide a "bone bonding" material. The material is produced in such a manner as to provide irregular pores between 100 and 250 microns in size.

The devices described in the above-referenced U.S. patents require multiple components to be made and either placed separately in the body or pre-assembled, resulting in a complicated manipulation at the time of implant in the first case or the danger that the juncture between device components will separate post-implantation in the others.

Furthermore, these device lack a macroarchitecture or overall design that allows for the diffusion of oxygen, nutrients, and growth factors, in and out of the area in addition to a microarchitecture which creates a microenvironment which enhances cell growth and tissue regeneration.

It is therefore an object of the present invention to overcome these shortcomings, by providing a device for seeding and culturing of cells within defined regions of the device, with a pore size and porosity promoting selecting cell attachment and proliferation.

It is a further object of the present invention to provide devices which can provide mechanical support and integrity after implantation.

It is a still further object of the present invention to provide such devices which are completely biodegradable.

SUMMARY OF THE INVENTION

The devices disclosed herein are composite implantable devices having a gradient of one or more of the following: materials, macroarchitecture, microarchitecture, or mechanical properties, which can be used to select or promote attachment of specific cell types on and in the devices prior to and/or after implantation. In various embodiments, the gradient forms a transition zone in the device from a region composed of materials or having properties best suited for one type of tissue to a region composed of materials or having properties suited for a different type of tissue.

The devices are made in a continuous process that imparts structural integrity as well as a unique gradient of materials in the architecture. The gradient may relate to the materials, the macroarchitecture, the microarchitecture, the mechanical properties of the device, or several of these together. The devices disclosed herein typically are made using solid free form processes, especially three-dimensional printing process (3DP™). Other types of solid free-form fabrication (SFF) methods include stereo-lithography (SLA), selective laser sintering (SLS), ballistic particle manufacturing (BPM), and fusion deposition modeling (FDM). The device can be manufactured in a single continuous process such that the transition from one form of tissue regeneration scaffold and the other form of tissue regeneration scaffold have no "seams" and are not subject to differential swelling along an axis once the device is implanted into physiological fluid.

In one embodiment for repair or replacement of bone, a gradient is formed of osteogenic and osteoconductive materials, such as calcium phosphates, to materials which are synthetic biocompatible polymers, such as poly(alpha) esters, which are particularly well suited for attachment of cells and controlled biodegradation. In another embodiment, the devices have a gradient in macroarchitecture. The macroarchitecture, or overall shape, can be of a design which allows fluid flow through and/or around one region and a different shape in another region with a gradient from one shape to the other. In another embodiment, the microarchitecture may be from an osteoinductive system of interconnected pores to a system of staggered channels inductive to chondrocyte colonization. In another aspect, the gradient may relate to mechanical properties such as tensile or compressive strength. The gradient of properties may be from that which is suitable for weight bearing loads to one which is suitable for soft tissue regeneration.

In another embodiment, materials such as growth factors, which selectively encourage or enhance the growth or differentiation of cells that form tissues, can be incorporated on or in the device. A particularly favored method of fabricating the devices includes incorporating the factors in the structure of the device.

BRIEF DESCRIPTION OF THE DRAWINGS

FIG. 2 shows a composite device for regeneration of cartilage which is implantable into bone.

FIGS. 3a–g are cross-sectional (two-dimensional) shapes of the implantable devices.

FIG. 4 are schematics of a composite device (FIG. 4f) of layers (FIGS. 4a–e), showing a sectional view of the staggered channel design in FIG. 4g (the dark regions represent polymer walls).

FIGS. 5a–f show the channel design of cartilage devices made by layering sections with different channel sizes and openings formed using masks to guide the deposition of solvent, chloroform, which solidifies and binds the polymer together (FIGS. 5a–e) to form a single composite (FIG. 5f).

DETAILED DESCRIPTION OF THE INVENTION

Figure 1:
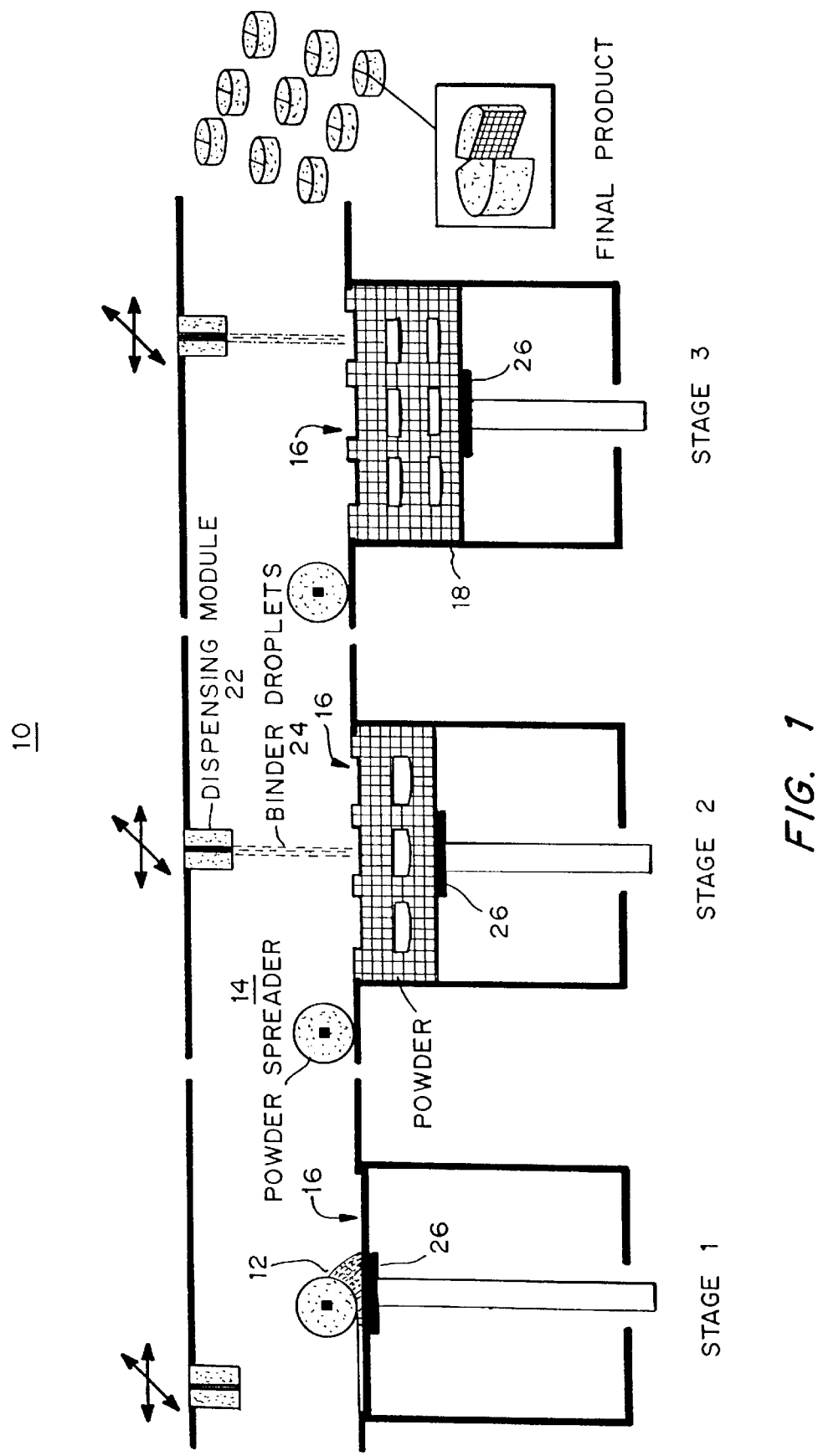
FIG. 1 is a schematic view of the process of three-dimensional printing to make medical devices.

Three-dimensional devices with unconventional microstructures and macroarchitecture have been developed, which can be seeded and implanted immediately, seeded in an extracorporeal system prior to placement in the body, or implanted and seeded/or populated by ingrowth from adjacent tissue. The devices have advantages when applied to the construction of complex alloplasts or partial allografts designed for tissue regeneration at a physiological junction between two types of supporting tissue. For example, devices manufactured as described herein which include gradients or transition zones that are designed for use in creating a composite of bone and cartilage are not susceptible to delamination of the bone portion from the cartilage portion caused by differential swelling of the polymeric materials or other properties, such as the hygroscopic nature of, or osmotic pressure generated by the placement of dry materials in a fluid filled cavity or other fluid containing site in the body, due to the integral nature of the device.

I. Devices
A. Device Structure

The devices are constructed to maximize cell attachment, proliferation and/or differentiation as required for a particular purpose. The following variables can be manipulated to achieve the desired effect: macrostructure, chemical composition, microstructure including porosity, pore size (diameter), surface modifications such as surfactants and cell attachment peptides, incorporation of bioactive agents, flow properties (i.e., channels that direct and control fluid flow through and within the device), and structural elements on or in the device. Manipulation of the printing parameters and powder characteristics allow the design and fabrication of macroarchitecture, microarchitecture, and internal and surface characteristics. "Macroarchitecture" is used herein to mean the overall shape of the device, which is on the order of millimeters to centimeters in dimension and with defined shape. The term "microarchitectural features" is used herein to mean the internal structure that is preconceived and built into the device. Fine features, such as tortuous interconnected pores and surface patterning, are properties of the materials, processing, and finishing, but are not necessarily placed by design or by the three-dimensional printing process.

The devices disclosed herein are a composite produced as a single part. The device has an overall shape that when placed in the body will compress slightly while allowing structural features for fluid movement within and without the device to be maintained, with channels and pores, suitable for implantation in the body at an interface between two types of tissues. One portion, such as the bone region of the composite device described herein, is specifically designed to address several functions. One of these is to encourage the migration of the blood and marrow-bourne tissue forming elements around and through the device, to maximize the surface-area-to-volume ratio in order to promote bone ingrowth, and to maximize compressive and torsional strength in order to provide the mechanical integrity needed to withstand the force of implantation. Minimization of material without sacrificing integrity of the device is considered desirable whenever possible in order to decrease the cost of goods required in production as well as to minimize the introduction of foreign substances into the body which could potentially evoke an immune response and which releases degradation by-products.

The overall shape of the device is such that the device functions to allow the continued flow of dissolved nutrients in biological or biocompatible fluids through and around the device, thus minimizing the possibility of pressure differential across the device being formed by gas, fluid or temperature gradients. The device contains geometry, pores, and fluid communication channels that are conducive to cell migration, attachment, growth, and differentiation. These features can be manipulated to selectively populate a particular region(s) of the device with different cell types, or to allow ingrowth into one region, while promoting cell attachment and proliferation in another. In this way, the device can facilitate the regeneration of the complex supporting tissue interfaces that are characteristic of, for example, the cartilage coated surface of a long bone at the synovial interface. As demonstrated by the example, these devices can be engineered to allow and encourage growth of both osteogenic cells and chondrocytes, both of which are part of a naturally occurring cartilage-bone interface.

Channels bounded by walls and consisting of substantially straight passageways of defined width, length, and orientation are a microarchitectural feature of the devices described herein. Staggered channels extending through the device and offset by 90° in different layers of the device are one particularly preferred embodiment. Staggering the channel and walls increases the strength of the device relative to a straight through channel design. The width of the channels can range from about 150 to 500 microns, with 250 microns preferred, in order to maximize the surface area available for cell seeding without compromising structural integrity or homogeneity of tissue formation.

In addition, the channels facilitate the transport of nutrient to the cells and removal of cellular by-products and polymer degradation by-products which all may occur whether the device is colonized by cells before or after implantation in the body. The unique macroscopic staggered channels are designed to allow chondrocytes to contact the device throughout the thickness of the device not only superficially. This is important due to the limited migration capacity of the chondrocytes; the migration distances of this cell type being less than about 2 mm. Thus, when the device is seeded extracorporally, the chondrocytes may be placed directly into the center of the device.

The porosity of a device will control the flow of nutrients to the colonizing cells as well as the surface area available for cellular attachment. Studies have shown that pores of a minimum diameter of 60 microns or greater are required for angiogenesis in highly vascularized tissue, such as bone. It is already known in the art that the porosity of the devices fabricated from powders or synthetic polymers or polymers and inorganic particles can be manipulated by incorporating "sacrificial" materials, such as sodium chloride, into the material. U.S. Pat. No. 5,514,378 teaches methods of dispersing salt particles in a biocompatible polymer solution, evaporating the polymer solvent and leaching the salt from the formed composite to create a porous membrane.

The devices are typically formed using synthetic polymeric materials. The device can include resorbable and/or non-resorbable materials, which can be positioned in various portions of the device during the manufacturing process. For a device to replace adjoint or other cartilage-bone composite , the materials forming one region are preferably osteoconductive and those materials forming a different adjacent region are preferably permissive to chondrocyte growth and maturation. Bioactive materials, such as growth factors, can be incorporated on or in the device to select for growth, differentiation or proliferation of a particular cell type.

Inserts in the device can also be used to manipulate cell attachment, proliferation and/or differentiation. For example, an insert with a first portion designed to support cartilage healing and regeneration, and a second portion designed to anchor in and support bone regeneration, can be incorporated into a device for use in treating osteochondral defects. In this example, described in more detail below, the device is fabricated in a continuous process as a single part in which three regions, distinct in intent, design, and composition, are present: 1) a cartilage portion, 2) a bone portion and 3) a transition zone adjacent to and connecting both the cartilage and bone portions. The cartilage portion is about 90% porous composed of synthetic polyester polymers containing staggered macro-channels of about 250 microns in diameter. The bone portion is from 25 to 55% porous and generally composed of both synthetic polymer and osteoconductive material in a shape permissive of fluid and gas flow at the outer edge of the device while maintaining contact with the host tissues.

The transition zone, which is adjacent to both the cartilage and the bone portions, forms a gradient in porosity from close to that of the bone or more dense portion to close to that of the cartilage or least dense portion. The transition zone may also form a gradient in polymer composition, from that of the bone portion to that of the cartilage portion, where the polymer is a copolymer and the ratio of monomers is different for the bone versus the cartilage portions, or the portions are formed of two different polymers and the transition zone is a blend or copolymer of the two polymers. The transition zone may also include a shape gradient or have a region which has an outer shape like the bone portion near the bone portion and a region with an outer shape that is substantially round or similar to the cartilage portion in the region nearest the cartilage portion.

Surface finish is governed by the physical characteristics of the materials used as well as the build parameters. These factors include particle size, powder packing, surface characteristics of the particles and printed binder (i.e. contact angle), exit velocity of the binder jet, binder saturation, layer height, and line spacing. Interaction of the binder liquid with the powder surface, in particular, can be controlled carefully to minimize surface roughness. In a case where the binder becomes wicked out in a large area, the feature size control may be difficult, resulting in a rough surface.

B. Device Composition

The device is manufactured using natural or synthetic structural materials that have inherent ability to encourage cell attachment, such as calcium phosphates, and provide mechanical integrity in terms of tensile strength and compressibility. The materials must be amenable to milling and sieving to produce specific particle sized powders, spreading of powder, and binding with solvent. Free powder must be removable from the device post-fabrication.

Particle Size

Materials to be used in the powder bed, if not naturally or otherwise available as substantially uniform particles, must be processed to achieve such. Synthetic polymer products used are subjected to cryogenic milling using, for example, an ultra-centrifugal mill (Model ZM100; Glen Mills, Clifton, N.J.) with liquid nitrogen. Analytical milling using such mills as the Model A20, Janke and Kunkel GmbH, Germany, is another preferred technique. Once milled the powders are vacuum dried.

Sieving of the milled material is performed to produce uniformly sized particles of a minimum and maximum size. The maximum particle size will therefore also be a function of the screen used. Screens of about 30 micron mesh are common and other screens of larger mesh may also be employed with satisfactory results. Screens may be stacked on a vibrating sifter-shaker (Model AS200, Retsch, Haan, Germany). Other sizes are described in the following examples.

Polymers

The preferred materials used in the manufacture of the devices described herein are biocompatible, bioresorbable over periods of weeks or longer, and generally encourage cell attachment. The term "bioresorbable" is used herein to mean that the material degrades into components which may be resorbed by the body and which may be further biodegradable. Biodegradable materials are capable of being degraded by active biological processes such as enzymatic cleavage. Other properties desirable for materials to be used in the manufacture of the devices described herein include (1) solubility in a biologically acceptable solvent that can be removed to generally accepted safe levels, (2) capability of being milled to particles of less than 150 microns, and (3) elasticity and compressive and tensile strength.

Synthetic polymers which have been found to be particularly suited to the present use include: poly(alpha)esters, such as: poly(lactic acid) (PLA) and poly(DL-lactic-co-glycolic acid) (PLGA). Other suitable materials include: poly($\epsilon$-caprolactone) (PCL), polyanhydrides, polyarylates, and polyphosphazene. Natural polymers which are suitable include: polysaccharides such as cellulose, dextrans, chitin, chitosan, glycosaminoglycans; hyaluronic acid or esters, chondroitin sulfate, and heparin; and natural or synthetic proteins or proteinoids such as elastin, collagen, agarose, calcium alginate, fibronectin, fibrin, laminin, gelatin, albumin, casein, silk protein, proteoglycans, Prolastin, Pronectin, or BetaSilk. Mixtures of any combination of polymers may also be used. Preferred synthetic polymers include: poly(hydroxy alkanoates), polydioxanone, polyamino acids, poly(gamma-glutamic acid), poly(vinyl acetates), poly(vinyl alcohols), poly(ethylene-imines), poly(orthoesters), polypohosphoesters, poly(tyrosine-carbonates), poly(ethylene glycols), poly(trimethlene carbonate), polyiminocarbonates, poly(oxyethylene-polyoxypropylene), poly(alpha-hydroxy-carboxylic acid/polyoxyalkylene), polyacetals, poly(propylene fumarates), and carboxymethylcellulose.

Advantages of using polylactic acid/polyglycolic acid (PLA/PLGA) polymers include: clinical experience and acceptance and ease of processing. A disadvantage is the production of acidic degradation products during degradation. However, provision for removal of acidic degradation products, along with other device generated or naturally generated toxins inherently produced during tissue healing or regeneration can be handled by the device design. PLGA 75:25 degrades rapidly in the body (4 to 5 months) but not as quickly as D,L-PLGA 50:50 (one to 2 months). On the other hand, other polymers with more slowly degrading properties may be blended with PLGA to produce a device capable of maintaining some physical properties for longer periods of time.

Osteoconductive materials include: ceramics such as hydroxyapatite (HA), tricalcium phosphate (TCP), calcium phosphate, calcium sulfate, alumina, bioactive glasses and glass-ceramics, animal derived structural proteins such as bovine collagen, and demineralized bone matrix processed from human cadaver bone. Commercially available materials include: ProOsteon 500 (Interpore International), BoneSource (Orthofix) and OSTEOSET (Wright Medical Technology), Grafton Gel, Flex, and Putty (Osteotech), and Collagraft (Zimmer).

Hyaluronic acid esters of benzyl or ethyl alcohol have suitable mechanical and degradation properties for use as either cartilage or blood vessel scaffolds and release few degradation products. Hyaluronic acid is present in high concentrations in developing tissues and may confer some potential benefits biologically. Hyaluronate ester powder generation should be possible by the techniques of cryogenic milling or coacervation. Polyethylene oxide (PEO) is available in a wide range of molecular weights and may be used as a blending agent to modify the degradation properties of the polyesters and hyaluronic acid esters.

Inorganic particles such as sodium chloride or tricalcium phosphate may be mixed with the polymer particles in the powder bed.

Polymer Solvents

The printing solution used may be a solvent for the polymer or contain a binder and may contain one or more dissolved additional polymers or other substances desired to be incorporated into the component. Preferred solvents are: water, chloroform, acetone, and ethanol.

The binder can be a solvent for the polymer and/or bioactive agent or an adhesive which binds the polymer particles. Solvents for most of the bioerodible polymers are known, for example, chloroform or other organic solvents. Organic and aqueous solvents for the protein and polysaccharide polymers are also known, although an aqueous solution is preferred if required to avoid denaturation of the protein. In some cases, however, binding is best achieved by denaturation of the protein. The binder can be the same material as is used in conventional powder processing methods or may be designed to ultimately yield the same binder through chemical or physical changes that take place in the powder bed after printing, for example, as a result of heating, photopolymerization, chemical cross-linking, or catalysis.

Incorporation of Auxiliary Materials or Bioactive Agents

Surface chemistry modifiers or biological factors or growth factors can be positioned on or in the device, which can be releasable in a physiological environment for the purpose of stimulating cell attachment, growth, maturation, and differentiation in the area of the device. Those bioactive agents which can be directly dissolved in a biocompatible solvent are highly preferred. Examples generally include proteins and peptides, polysaccharides, nucleic acids, lipids, and non-protein organic and inorganic compounds, referred to herein as "bioactive agents" unless specifically stated otherwise. These materials have biological effects such as growth factors, differentiation factors, steroid hormones, cytokines, lymphokines, antibiotics, and angiogenesis promoting or inhibiting factors.

Bioactive agents also include compounds having principally a structural role, for example, hydroxyapatite crystals in a matrix for bone regeneration. The particles may have a size of greater than or less than the particle size of the polymer particles used to make the matrix.

It is also possible to incorporate materials not exerting a biological effect such as air, radiopaque materials such as barium, or other imaging agents for the purpose of monitoring the device in vivo.

In order to promote cell attachment, cell adhesion factors such as laminin, pronectin, or fibronectin or fragments thereof, e.g. arginine-glycine-aspartate, may be coated on or attached to the device. The device may also be coated or have incorporated cytokines or other releasable cell stimulating factors such as; basic fibroblast growth factor (bFGF), transforming growth factor beta (TGF-beta), nerve growth factor (NGF), insulin-like growth factor-1 (IGF-1), growth hormone (GH), multiplication stimulating activity (MSA), cartilage derived factor (CDF), bone morphogenic proteins (BMPs) or other osteogenic factors, anti-angiogenesis factors (angiostatin), In addition, either exogenously added cells or exogenously added factors including genes may be added to the implant before or after its placement in the body. Such cells include autografted cells which are derived from the patients tissue and have (optionally) been expanded in number by culturing ex vivo for a period of time before being reintroduced. Cartilage tissue may be harvested and the cells disaggregated therefrom, and cultured to provide a source of new cartilage cells for seeding the devices. The devices may also be seeded with cells ex vivo and placed in the body with live cells attached thereto.

DNA of a gene sequence, or portion thereof, coding for a growth factor or other of the auxiliary factors mentioned above may also be incorporated into the device or added to the device before or after placement in the body. The DNA sequence may be "naked" or present in a vector or otherwise encapsulated or protected. The DNA sequence may also represent an antisense sequence of a gene or portion thereof.

There are essentially no limitations on the bioactive agents that can be incorporated into the devices. Those materials which can be processed into particles using spray drying, atomization, grinding, or other standard methodology, or those materials which can be formed into emulsions, microparticles, liposomes, or other small particles, and which remain stable chemically and retain biological activity in a polymeric matrix, are preferred.

C. Methods of Manufacturing Devices

The preferred methods for manufacturing the devices are solid free-form fabrication (SFF). SFF methods can be used to selectively control composition within the build plane by varying the composition of printed material. The SFF methods can be adapted for use with a variety of polymeric, inorganic and composite materials to create structures with defined compositions, strengths, and densities, using computer aided design (CAD). This means that unconventional microstructures, such as those with complicated porous networks or unusual composition gradients, can be designed at a CAD terminal and built through an SFF process such as 3DP.

Three Dimensional Printing

3DP uses a process of spreading powder and depositing binder onto a powder bed. Three-dimensional printing is described by Sachs, et al., "CAD-Casting: Direct Fabrication of Ceramic Shells and Cores by Three-dimensional Printing: Manufacturing Review 5 (2), 117–126 (1992) and U.S. Pat. No. 5,204,055, the teachings of which are incorporated herein. Suitable apparatuses include both those with a continuous jet stream printhead and a drop-on-demand (DOD) printhead. 3DP can be used to create a porous bioerodible matrix for use as a medical device as taught in U.S. Pat. Nos. 5,490,962 and 5,518,680 to Cima, et al., the teachings of which are incorporated herein by reference.

A continuous-jet head provides for a fluid that is pressure driven through a small orifice. Droplets naturally break off at a frequency that is a function of the fluid's properties and the orifice diameter. Multiple jet heads are preferred. A DOD printhead utilizes individual solenoid valves that run at frequencies up to 1.2 kHz. Fluid is pressure driven through these valves, and a small orifice is downstream of the valves to ensure accurate and repeatable droplet size.

Both raster and vector apparatuses can be used. When using DOD, a raster apparatus provides that the printhead goes back and forth across the bed with the jet turning on and off. A continuous-jet head is always on, and a vector apparatus is used similar to an x-y printer. 3DP is used to create a solid object by ink-jet printing a binder onto selected areas of sequentially deposited layers of powder or particulates, as shown in FIG. 1, discussed in more detail below. In the following description, the terms "powder" and "particulates" are used interchangeably. Each layer is created by spreading a thin layer of powder over the surface of a powder bed. In a preferred embodiment, a moveable powder piston is located within a cylinder, with a powered roller to deliver dispensed powder to a receiving platform located adjacent to the powder feeder mechanism.

The feed piston is raised a predetermined amount for each increment of powder delivery. The roller then sweeps across the surface of the powder feeder cylinder and deposits it as a thin layer across the receiving platform immediately adjacent to the powder feeder. The powder feeding piston is then lowered as the roller is brought back to the home position, to prevent any back delivery of powder. The powder piston and cylinder arrangement can also consist of multiple piston/cylinders located in a common housing, which could be used to dispense multiple powders in the following sequence:

1. Line up the first desired powder cylinder with the rolling/delivery mechanism;
2. Raise incrementally the movable position piston to deliver an incremental amount of powder;
3. Activate the roller to move the powder to a receiving platform;
4. Lower the powder piston driving mechanism;
5. Laterally slide the powder feeder housing so that the next desired powder cylinder is lined up with the delivery mechanism;
6. Repeat steps 2, 3, 4 and 5; and
7. Continue for as many different powders and/or powder layers as required.

This method of powder feeding can be controlled manually or be fully automated. Cross contamination of different powders is minimized since each powder is contained in its own separate cylinder. One of the advantages to this method is that only one piston raising/lowering mechanism is required for operation, regardless of the number of powder cylinders. By raising the powder for delivery rather than dropping it from above, problems associated with gravity based delivery systems such as "ratholing", incomplete feed screw filling/emptying and "dusting" with the use of fine powders is eliminated or minimized since only enough energy is introduced to move the powder up an incremental amount. The powder feeder housing, with its multiple cylinders and pistons, can also be designed as a removable assembly, which minimizes changeover times from one powder system to another.

The powder bed is supported by a piston that descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three-dimensional structure. The unbound powder supports temporarily unconnected portions of the component as the structure is built but is removed after completion of printing.

The 3DP process is shown schematically in FIG. 1, wherein a 3DP apparatus is indicated generally by the number 10. Powder 12 is rolled from a feeder source (not shown) in stage I with a powder spreader 14 onto a surface 16 of a build bed 18. The thickness of the spread layer is varied as a function of the type of dosage form being produced. Generally, the thickness of the layer can vary from about 100 to about 500 microns, and more typically from 100 to about 200 microns. The printhead 22 then deposits the binder (fluid) 24 onto the powder layer and the build piston 26 is lowered one layer distance. Powder is again rolled onto the build bed 18 and the process is repeated until the dosage forms are completed (stages 2 and 3 of FIG. 1). The droplet size of the fluid is from about 50 to about 500 microns in diameter and more typically greater than 80 microns. Servomotors (not shown) are used to drive the various actions of the apparatus 10.

Construction of a 3DP component can be viewed as the knitting together of structural elements that result from printing individual binder droplets into a powder bed. These elements are called microstructural primitives. The dimensions of the primitives determine the length scale over which the microstructure can be changed. Thus, the smallest region over which the concentration of bioactive agent can be varied has dimensions near that of individual droplet primitives. Droplet primitives have dimensions that are very similar to the width of line primitives formed by consecutive printing of droplets along a single line in the powder bed. The dimensions of the line primitive depend on the powder particle dimension and the amount of binder printed per unit line length. A line primitive of 500 micron width is produced if an inkjet depositing 1.1 cc/min of methylene chloride is made to raster at 8"/sec over the surface of a polycaprolactone (PCL) powder bed with 45–75 micron particle size. Higher printhead velocities and smaller particle size produce finer lines. The dimensions of the primitive seem to scale with that calculated on the assumption that the liquid binder or solvent needs to fill the pores of the region in the powder which forms the primitive.

Finer feature size is also achieved by printing polymer solutions rather than pure solvents. For example, a 10 wt. % PCL solution in chloroform produces 200 micron lines under the same conditions as above. The higher solution viscosity slows the migration of solvent away from the center of the primitive.

The layers become hardened or at least partially hardened as each of the layers is laid down. Once the desired final configuration is achieved and the layering process is complete, it may be desirable in some applications that the form and its contents be heated or cured at a temperature selected to further promote binding of the powder particles. In the case of matrices for implantable devices built from biocompatible materials, whether or not further curing is required, the loose unbonded powder particles may or may not be removed using a suitable technique such as ultrasonic cleaning, to leave a finished device.

The solvent drying rate is an important variable in the production of polymer parts by 3DP. Very rapid drying of the solvent tends to cause warping of the printed component. Much, if not all, of the warping can be eliminated by choosing a solvent with a low vapor pressure. Thus, polycaprolactone (PCL) parts prepared by printing chloroform have nearly undetectable amounts of warpage, while large parts made with methylene chloride exhibit significant warpage. It is often convenient to combine solvents to achieve minimal warping and adequate bonding between the particles. Thus, an aggressive solvent can be mixed in small proportions with a solvent with lower vapor pressure.

Significant amounts of matter can be deposited in selective regions of a component on a 100 micron scale by printing solid dispersions or solid precursors through the ink-jet printheads. Hundreds of jets can be incorporated into the process. The large number of individually controlled jets makes high rate 3DP construction possible.

3DP requires the use of polymer particles or powder. The minimum final feature dimension of the work product will be dependent on the initial particle size of the powder material used. That is, the process of joining at least two particles by printing a drop of solvent thereon means that the minimum feature size is approximately twice the particle size. Aggressive solvents tend to nearly dissolve the particles and reprecipitate dense polymer upon drying. The time for drying is primarily determined by the vapor pressure of the solvent. There is a range from one extreme over which the polymer is very soluble, for example, 30 weight percent solubility, which allows the polymer to dissolve very quickly during the time required to print one layer, as compared with lower solubilities. The degree to which the particles are attached depends on the particle size and the solubility of the polymer in the solvent. Fine powder is more quickly dissolved than powder with larger particle size. Furthermore, relatively large particles may not dissolve completely before the solvent binder evaporates.

In the preferred embodiment described herein, the devices include either a gradient or a transition zone, which can itself be a gradient. The gradient can be a gradient of materials or material mixtures. Using a gradient of materials allows the physical properties of the resulting structures to change gradually, thereby mitigating large discontinuities which can lead to disruption of or performance failure by the device. Such physical properties of the materials include thermal expansion coefficient, elasticity, and swelling.

There are two principal methods for incorporation of bioactive agent into the device: as a dispersion within a polymeric matrix and as discrete units within a discrete polymeric matrix. In the first method, the bioactive agent preferably is applied in the polymer particle binder; in the second method, the bioactive agent is applied in a non-solvent for the polymer particles.

The selection of the solvent for the bioactive agent depends on the desired mode of release and the compatibility of the bioactive agent in the solvent. The solvent is selected to either dissolve the matrix or is selected to contain a second polymer which is deposited along with the bioactive agent. In the first case. the printed droplet locally dissolves the polymer powder and begins to evaporate. The bioactive agent is effectively deposited in the polymer powder after evaporation since the dissolved polymer is deposited along with the agent. The latter case, where both the drug and a polymer are dissolved in the printed solution, is useful in when the powder layer is not soluble in the solvent. Binding is achieved by deposition of the binder, in this case the polymer, at the necks between the powder particles so that they are effectively bound together along with the bioactive agent.

Devices may be fabricated with bioactive-rich regions within the device. In this case, multiple printheads are used to deposit active containing solvent in selected regions of the powder bed. The remaining volume of the desired device is bound with pure solvent deposited by a separate printhead. The devices also simply may be coated with the bioactive agent or have the agent placed therein or thereon. The bioactive agent may be covalently or noncovalently attached to the device.

Other SFF Methods

Other types of solid free-form fabrication (SFF) methods may be adapted to make the devices described herein. These methods include stereo-lithography (SLA), selective laser sintering (SLS), ballistic particle manufacturing (BPM), and fusion deposition modeling (FDM).

Stereolithography is based on the use of a focused ultraviolet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer.

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers.

FDM employs an x-y plotter with a z motion to position an extrudable filament formed of a polymeric material, rendered fluid by heat or the presence of a solvent The materials and construction of devices including a transition zone and/or gradient(s) will be further understood by reference to the following non-limiting examples.

EXAMPLE 1

Use of Three-dimensional Printing Techniques to Construct a Composite Device

A bone replacement part designed to assure mechanical strength, density, and weight similar to that of bone logically may be assumed to require the appearance of cancellous bone in both internal and external structure. However, as discussed above, the healing process occurs in several stages and bone formation requires, in some cases, that cellular precursors undergo migration and differentiation before new bone is formed. Thus, the objective of a bone tissue or cartilage tissue healing device is not to imitate the configuration of the final tissue structure but rather to encourage and enhance the natural tissue formation process while contributing mechanical strength in the area to be regenerated. 3DP, like any process, has limitations imposed by the nature of the materials and the apparatus used.

FIG. 2 is a schematic of an implantable composite device for implantation into a bony site for regeneration of cartilage. The dark regions in the layers are holes that create the staggered channels. There are 22 layers for bone, having the cloverleaf design, to a thickness of 5 mm. Layers 23–28 are transition layers, then layers 29–38, forming a thickness of 2 mm, are for formation of cartilage. Layers 1–26 use a 1 cm cloverleaf stencil, and layers 27–38 use the 1 cm disk stencil. Two layers of each design are made for the cartilage region.

FIGS. 3a–g show the shapes contemplated for the two-dimensional cross section of a portion of the device, typically the portion intended to reside within bone. Designs contemplated for the bone portion of the composite device were analyzed on the basis of selected criteria including compressive strength, surface area available for cell adhesion, and ease of fabrication. Other criteria such as the ability to fabricate the device using masking rather than computer controlled printing were also considered for initial ease of prototype production. The specific criteria is shown in Table 1.

TABLE 1

Decision Matrix for Design of Bone Portion

| | Tube | Coil | Clover | Inverted or Negative Clover | Honey-comb | Slots |
|---|---|---|---|---|---|---|
| Compression | Good | Good | Good | Good | Good | Good |
| Shear | Good | Good | Good | Good | Good | Good |
| Torsional Stiffness | Good | Good | OK | Good | Good | Good |
| Radii | Good | Good | Good | Good | Good | Good |
| Perimeter | OK | Good | OK | OK | Good | Good |
| Attachment Length | Good | Good | OK | Good | Good | Good |
| Mask Friendly | OK | No | Yes | No | No | No |

The two designs having the highest number of positive features are the hollow cylinder and the clover design, both of which can be fabricated with masks. The honeycomb design is another candidate for fabrication using inkjet printheads for drop-on-demand of organic solvents. The honeycomb design enables maximizing both surface area and void volume for tissue ingrowth and biological interaction while maintaining high uniaxial strength.

EXAMPLE 2

Determination of Optimal Pore Size and Porosity

The devices described herein must be porous but retain strength, as well as be composed of osteoconductive materials. Therefore, the relationship between the initial salt content of the powder mixture used and the final product characteristics must be closely matched. Fabrication of structures with designed pore or channel structures is a challenging task even with additive manufacturing processes such as 3DP. Structures with radial or vertical channels of hundreds of microns in diameter can be fabricated; however, the formation of narrower and tortuous internal structures is best affected by the use of a sacrificial material. One common practice in the construction of tissue engineering matrices is the use of mixtures of water soluble particulates (sodium chloride) with non-water soluble polymers dissolved in a solvent to fabricate specimens. The salt particles can be leached out of the device with water to reveal a porous structure. While this technique is useful in fabricating a network of pores, control of pore architecture is lost.

A modified leaching protocol was adopted to approximate more closely the seeding and culture conditions to which the devices would be subjected. $CO_2$ dried samples were placed into a Nalgene bottle that contained a minimum of 20 ml of water per sample. The bottle was placed onto an orbital shaker (model 3527, Lab-Line Environ, Melrose Park, Ill.) at 100 rpm and 37° C. The water was replaced every hour. After five hours, the NaCl content in the solution was evaluated using silver nitrate for white precipitate that indicates NaCl. If NaCl was detected, leaching was continued until none was detected. Samples were removed, blotted dry, and placed into a vacuum desiccator overnight to complete drying. Leaching can also be performed using a ball mill apparatus at room temperature.

The porosity of the devices was determined by the mass loss upon leaching the NaCl out of the device. This was done by measuring the dry mass of the devices before and after leaching.

The porosity was varied between the two tissue specific regions of the device. In the region designed specifically to enhance cartilage regeneration, the porosity was maximized ($\geq 90\%$) to promote cell attachment and proliferation and allow space for formation of extracellular matrix. Highly porous structures have a high surface-to-volume ratio. The surface area maximizes available sites for cell attachment while minimizing the amount of material used. Minimizing material, besides allowing space for living components and promoting homogeneous formation of tissue, also minimizes the non-living foreign material which can cause immune response and produces potentially detrimental degradation by-products.

In the region of the device designed specifically to be implanted in bone, the device was less porous in order to provide for more mechanical strength and to discourage attachment of chondrocytes. The materials selected for this region are slowly degrading bioresorbable materials with an initially large pore size created by leaching out salt particles of 125 microns or greater. A gradient of porosities is achieved by altering the salt content of the powder bed in successive layers.

Poly($\epsilon$-caprolactone) (PCL) was used as the polymer. The PCL as received (Birmingham Polymers, lot D961 57, 200,000 MW) was cryogenically milled and sieved to a particle size below 150 $\mu$m. There was approximately a 10% yield from the milling process. Optical micrographs revealed most particles to be near the upper size limit. Particle size analysis (Amherst Process Instruments, Amherst, Mass.) showed the average size to be 111±2 $\mu$m assuming a spherical shape. Many particles were oblong and longer than the upper screen size, indicating a large degree of shear during the milling process.

Powder mixtures were prepared with the following compositions:

1. 100% PCL [<150 μm]
2. 90% NaCl [125–150 μm], 10% PCL [<150 μm]
3. 90% NaCl [125–150 μm], 5% PCL [<150 μm], 5% TCP [38–150 μm].

Print Tests—The pure PCL powder and powder mixtures were subjected to a set of standard testing protocol procedures to determine their suitability for use with the 3DP process. These procedures included a succession of spread, drop, binder, line, ribbon, and wall tests.

Spread test—The pure PCL powder spread relatively poorly due to the very low packing density. The two 90% NaCl mixtures spread in a comparable manner as other polyester powders used with the process. Layers as small as 200 μm were easily spread.

Drop test—Chloroform drops, 10 μl volume, were deposited onto a bed of each of the powders. Wettability was good and bleeding was minor for all powders tested. Pure PCL powder showed excellent binding strength with the solvent. The 90% NaCl powder mixtures produced low strength drop primitives. The primitives had relatively low hardness and were pliable. The primitives from the 5% TCP mixture were loosely bound and had poor strength.

Binder test—The use of chloroform with the continuous jet nozzle was found to produce a steady flow rate of 1.2 ml/min at 20 psi.

Line test—Base powder beds were prepared 2 mm deep, and chloroform binder flow was established at 1.2 ml/min. Lines of velocities between 0.75 m/s and 1.5 m/s were executed on pure PCL powder and the two powder mixtures. Ballistic and bleeding effects were minor at all print speeds. The smallest line generated using pure PCL powder was 480 μm in diameter, and the largest line was 670 μm in diameter. Line size could not be measured for the 90% NaCl powders because the fragile samples could not be retrieved from the powder bed, even when printed at lower speeds.

Ribbon test—Base powder beds were prepared and binder flow was established as for the line test. Ribbons 20 mm in length and 3 mm in width were fabricated with all of the powder mixtures using velocities between 0.75 m/s and 1.5 m/s, and line spacings between 75 and 150 μm. Optimal parameters were chosen such that bleeding was minor and a ribbon sample could be recovered from the bed.

Optimal parameters were 125 cm/s velocity and 100 μm line spacing for pure and 10% PCL powders, and 100 cm/s velocity and 100 μm line spacing for the 5% PCL mixture. Ribbons fabricated with the pure PCL powder showed excellent strength; however, particle dissolution was incomplete. Double-printing the ribbon yielded particles that were more extensively dissolved and displayed a rubbery nature. Double-printing is applied, in general, when processing large polymer particles (>100 μm) for enhanced dissolution and improved bonding.

Wall test—The data from this test in conjunction with the line test was used to determine the minimum feature size and optimum printing resolution that could be expected with the powder and binder. This final test included fabricating walls by printing a set of lines on multiple layers. Walls of one, two, and three adjacent line widths were fabricated with the 90% NaCl: 10% PCL mixture. The horizontal spacing between adjacent lines within the walls was 100 μm and the vertical layer spacing was 180 μm. The print velocity was 125 cm/s, and the chloroform binder flow rate was 1.2 ml/min. The resulting wall thickness was 0.52, 0.58, and 0.79 mm for walls of single-, double-, and triple-line widths, respectively. This indicates bleeding levels of between 250 and 290 μm both behind and ahead of the printed feature. These values are slightly higher than those typically encountered with other polyester powders. However, it is believed that this is due to the large polymer and NaCl sizes. Reducing the particle sizes should improve print resolution.

EXAMPLE 3

Mixtures of PLGA, CaP and NaCl to Make Porous Devices

Three powders: slow degrading PLGA (D,L-PLGA (85:15)), tri-calcium phosphate (CaP), and NaCl, mixed together, would not yield mechanically strong devices. Therefore, CaP and PLGA were coacervated with the NaCl. The NaCl was dissolved in a solvent and the CaP suspended in the polymer solution. A solution that is non-solvent for the polymer was then added, causing all three materials to precipitate out of solution in one homogeneous phase. The residual chloroform was removed from this material using supercritical $CO_2$, because liquid $CO_2$ was not appropriate for such a large mass.

The coacervated material was sealed in the vessel and chilled to 10° C. The vessel was filled with liquid $CO_2$ to a pressure of 750–800 psi. After filling the vessel, the outlet valve was opened to allow a 10 minute continuous vent at 20 SCFH. Following the vent period, the outlet valve was closed and the devices were held in liquid $CO_2$ for 5 minutes. The vessel was then heated to 40° C. (supercritical conditions) using an external water bath heater. As the temperature increased, the pressure also increased. The outlet valve was opened to maintain a maximum pressure of 1400 psi. The samples were maintained above 40° C. for 10 minutes, and then the vessel was vented at 10–20 SCFH.

The D,L-PLGA (85:15) used initially deformed under these conditions as well as milder liquid $CO_2$ conditions. This strongly indicated that the final products would not be able to withstand post-processing conditions needed to remove residual chloroform. In addition, this material also had to be milled to less than 150 μm for use in the three-dimensional printing process. Milling of this coacervated material in a small analytical mill with a cooling jacket caused it to discolor. The gray discoloration was believed to be either iron contamination from the mill or decomposed polymer. Energy dispersive X-ray spectroscopy analysis was used to determine that no significant amounts of iron were present in the milled coacervate. From this result, along with subsequent experience, it was determined that the polymer had decomposed during milling. L-PLGA (85:15) was used to avoid the problem of polymer decomposition during milling. L-PLGA, unlike D,L-PLGA, is crystalline and has a higher melting point. To verify that the coacervation process was successful, the ratio of tricalcium phosphate (CaP) to polymer was determined by ThermoGravimetric Analysis (TGA). A 10–50 mg sample of the material was placed in the TGA apparatus (Perkin-Elmer, Series 7, Norwalk, Conn.) and heated at 5° C./min to 500° C. At this temperature all polymer material had been vaporized and the sample had reached constant weight. By comparing results for CaP with coacervated CaP-PLGA samples, a polymer weight fraction of each sample was calculated. Initial TGA indicated that the ratio of materials recovered was consistent with the ratio of materials used.

EXAMPLE 4

Preparation of a Bone Device from a PLGA Coacervate

Polymer and bone composites were fabricated by three different methods: (1) mixing pure powders of bone and polymer in the powder bed in the desired ratios; (2) printing a polymer solution into a bed of bone powder; and (3) forming a powder which itself is a composite of bone and polymer.

Materials Poly-l-lactic acid (PLLA, Mw=50,000) and poly lactide-co-gglycolide (PLGA, Mw=115,000) from Boehringer-Ingleheim in the form of 1–3 mm granules were cryogenically milled using a centrifugal mill (Glen Mills, N.J.). The milling chamber was partially filled with liquid nitrogen, a slurry of liquid nitrogen and powder was introduced, and the milling commenced. The liquid nitrogen maintains the polymer temperature below the glass transition temperature (Tg) during the milling process. The processed powder was collected, dried in a vacuum oven for 24 hours, and mechanically sieved for 1 hour to classify the powder into distinct particle sizes.

Bovine cortical bone was sectioned into 3 to 5 mm blocks for cryogenic milling as described. The milled bone was dried and sieved with a yield of 50% bone powder in the 20–45 µm range and 15% less than 20 µm.

The approach of using a mixture of these two types of powders was found to be unfeasible because the interaction of the binder with the powder did not result in suitable bonding of particles when the particles are 45–75 µm. When the particles were under 20 µm, wicking of the fluid results in poor resolution.

Printing with dissolved polymer onto a bed of bone particles was feasible only for molecular weight polymers of low molecular weight (50,000) due to unacceptably high viscosity developed in solutions of sufficient concentration produced with higher molecular weight polymer. The use of less concentrated solutions and low molecular weight polymers in the printing solution would result in the strength of the product device being unacceptably low for bone regeneration.

The production of a bone and polymer coacervate was achieved using well known technology in the field of ceramic fabrication, that used to produce ceramic greenware. The process is similar to microencapsulation techniques. Particles, in this case bone rather than ceramic, are dispersed in the polymer solution in such a manner as to cause the bone particles to become coated with polymer and to remain suspended in the polymer solvent. The coated particles are precipitated into a uniform mass of material by addition of a non-solvent for the polymer. In the present case, bone powder (20–45 µm) was dispersed in a polymer solution (5–10% PLGA by weight in chloroform) to form a 1:1 mixture of bone and polymer. Sonication at 25 MHz for 5 minutes uniformly dispersed the bone particles. Isopropanol was then added to a final volume ratio of 3:1 of suspension:isopropanol to harden the polymer and produce the coacervate. The solid was collected, filtered, and dried under vacuum. The coacervate was then milled to produce bone particles and polymer typically in the 50 µm range.

The coacervate material was used in the powder bed with chloroform used as the printing material. The placement of the droplets was accomplished by using masks of thin stainless steel plates with laser-cut holes in the pattern desired to be printed. The material was used successfully to fabricate devices with defined channel architecture. The devices were approximately 50 weight percent bone and 60 volume percent bone. The compressive elastic modulus of the devices are about 50 GPa.

EXAMPLE 5

Porous Devices of Polymer and CaP Created by Salt Leaching

In this experiment, two compositions containing polymer and inorganic particles as tri-calcium phosphate (TCP) were compared. One composition was 35% NaCl and a 2:1 ratio of PLGA to TCP (35% porous);the other was 45% NaCl and a 3:1 ratio of PLGA to TCP (45% porous). To investigate the rate at which NaCl was leached out of the devices, two methods of calculating salt loss from the composition were used on devices leached in water using agitation produced either by a ball mill or an orbital shaker. The $CO_2$ dried samples were placed in 20 ml of water and placed either in a ball milling device (U.S. Stoneware, East Palestine, Ohio) or onto an orbital shaker (Model 3527, Lab-Line Environ, Melrose Park, Ill.) at 100 rpm and 37° C. The water was replaced each hour and the water removed from the devices monitored for residual salt by silver nitrate precipitation.

Elemental analysis was performed on bone devices leached by both methods in order to quantitate the extent to which NaCl had been removed from the compositions of the devices. In addition, the polymer, NaCl, water, and air volume fractions during leaching of bone devices were measured on device leached using the orbital shaker.

The results of the elemental analysis are shown in Table 2. The elemental data confirmed that leaching for longer periods was more effective at removing a greater fraction of NaCl. After 4 hours of leaching, the 35% porous samples contained 176±3 ppm of Sodium (n=3). After 5 hours of leaching, the 45% porous samples contained 0.5±0.1% of Sodium (n=3). These Sodium values indicate that only 0.04% and 1.3% NaCl remained in the devices after undergoing the leaching on an orbital shaker.

TABLE 2

| Elemental Analysis of Bone Devices after NaCl Leaching. | | | | |
| --- | --- | --- | --- | --- |
| Initial NaCl | Method & Time | PLGA (wt %) | TCP (wt %) | NaCl (wt %) |
| 35% | Theoretical | 67 | 33 | — |
| " | 3 hrs on ball mill | 62 | 28 | 7.4 |
| " | 4 hrs on shaker | 69 | 29 | 0.04 |
| 45% | Theoretical | 75 | 25 | — |
| " | 3 hrs on ball mill | 57 | 17 | 22 |
| " | 5 hrs on shaker | 76 | 22 | 1.3 |

Porosity calculations confirmed that these two batches lost 99% of the incorporated NaCl. After significant leaching, the ratio of PLGA to TCP was close to the theoretical value for both batches. This suggests that TCP was not being lost during the leaching process, and that a discontinuity in the porous network was not a concern at these NaCl loadings (i.e., 35 and 45 wt %).

A density measurement apparatus was used to measure the overall porosity of the devices. The calculations for the volume fractions. of each component included measurements of the buoyancy force, dry mass of the device, device dimensions, and densities of each material. Calculation of the volume fractions by this method proved unreliable. Several observations were made concerning the data. First, the water occupied a substantial fraction of the device even after only a half-hour of leaching. This indicated that the water infiltration was relatively rapid due to capillary and hydrophilic effects. Second, it confirmed that NaCl dissolution and/or diffusion was the rate-limiting step of leaching rather than the rate of water infiltration. These results suggest that water slowly displaced the NaCl as it was dissolved.

Results suggest that the 35% NaCl devices were fully leached after the seven-hour period; however, NaCl remained in the 45% NaCl devices even after seven hours of leaching. In both bone device batches, the void volume remained relatively constant during the entire leaching duration, with the final residual level being around 13%. This was an unexpected observation, considering water should have displaced all air and NaCl for leaching to be complete. Trapped air pockets may have been present in the samples. This may explain why some devices, such as the cartilage batches, float during leaching even though the densities of the polymer (1.3 g/cm$^3$) and NaCl (2.17 g/cm$^3$) are greater than that of water (1.0 g/cm$^3$).

The composition calculations derived from these measurements were not strictly comparable to that based on elemental analysis at all time points. The data at three hours correlated well despite the difference in leaching conditions, with the NaCl content at 6% for the 35% sample and 23% for the 45% sample. Discrepancy between the NaCl values occurred in the compositions calculated from the data for longer leaching periods. Possible sources of error in the water infiltration study include: 1) the devices may not have been fully dried in the dry weight measurements, 2) the device dimensions included stilts, 3) the assumption that the devices were perfect cylinders, and 4) the density values used for the polymer, NaCl, and TCP.

The results are consistent with NaCl dissolution and/or diffusion as the rate-limiting step of leaching rather than the rate of water infiltration. Furthermore, the silver nitrate assay was determined to be an easy and accurate predictor of complete leaching.

EXAMPLE 6

Mechanical Strength of Porous Devices Containing Inorganic Particles

The mechanical properties of bone device implants containing PLGA, TCP, and NaCl were investigated in this study. The L-PLGA used was an (85:15) copolymer of 242,000 MW (Lot D97157, Birmingham Polymers Inc.) milled to 38–150 µm. The TCP (Lot 95HO644, Sigma) was used in the 38–150 µm particle size range, and larger NaCl (Lot 965737, Fisher) in the 75–150 µm size was used, except for batch B5 which was 125–150 µm.

Samples of five different compositions as listed in Table 3 were fabricated to study the influence of porosity and inorganic content on tensile and compressive properties. The parameters used to fabricate the specimens are provided in Table 4. Combinations 1 through 4 were manufactured with Instruction A, and combination 5 was manufactured with Instruction B to reproduce more closely the actual device fabrication conditions. All samples were liquid $CO_2$ dried to remove residual chloroform and leached to remove NaCl before testing. American Society of Testing and Materials (ASTM) testing standards were adhered to when possible, but slight modifications were made to simplify the fabrication and testing process. Values for elastic modulus, yield strength, tensile strength, percent elongation, and compressive strength were obtained from load-displacement curves.

TABLE 3

Summary of Samples Produced for Mechanical Testing Study

| Batch | NaCl | L-PLGA | TCP | PLGA:TCP |
|---|---|---|---|---|
| B1 | 25% | 50% | 25% | 2:1 |
| B2 | 35% | 43% | 22% | 2:1 |
| B3 | 35% | 50% | 15% | 3.3:1 |
| B4 | 40% | 45% | 15% | 3:1 |
| B5 | 55% | 34% | 11% | 3:1 |

The correct composition of powder was placed into the powder bed to produce the number of samples needed. Double-sided tape was used to improve initial powder spreading, and three layers of stilts were constructed by skipping lines during printing. Stilts are parallel ridges formed in the powder bed prior to beginning the machine instructions for the actual workpiece which facilitate removal of the piece from the powder bed on the build platform. Samples were double-printed using Instruction A and single-printed with Instruction B. The tensile specimens were twenty layers, and the compression samples were sixty layers. After fabrication, the print plates were placed into a desiccator for 24 hours. Specimens were then placed into a nitrogen cupboard overnight to remove a majority of the chloroform.

TABLE 4

Fabrication Parameters Used

| Instruction A | Instruction B |
|---|---|
| Machine Version: MIT 3D Printer | Machine Version: TheriForm ™ |
| Flow rate: 1.2 ml/min | Flow rate: 1.2 ml/min |
| Reservoir pressure: 20 psi | Reservoir pressure: 20 psi |
| Print speed: 1.1 m/s | Print speed: 1.25 m/s |
| Line Spacing: 150 µm | Line Spacing: 125 µm |
| Layer heights: 200 µm | Layer heights: 200 µm |
| Stilt height: 300 µm | Stilt height: 300 µm |

Tensile Testing—Tensile testing specimens were fabricated with dimensions conforming to ASTM standard D 638–96. Custom-manufactured masks were used to generate samples of the appropriate dimensions as described in FIG. 2. An Instron Testing machine 4201 was used for both tensile and compression testing. Pneumatic grips (Instron type 2712) were used to hold the specimens in place with an external air pressure of 30 psi. This pressure produced some deformation of the wide section of the sample. To ensure good transfer of load from the grips to the specimen it was necessary to use a spacer on the far edge of the grips. A strain rate of 0.1 mm/min was applied on five different samples and load was recorded during the process. Displacement was measured using an extensiometer (Instron, Cat. no. 2620-826, travel +/−0.254 mm) with plasticine underneath. The initial cross-sectional area was used to aid in the following calculations. Young's modulus was calculated as the ratio of stress to strain before the material yielded. Tensile strength was found as the peak stress before fracture. Dimensions of the tensile testing specimens were as follows. LO=50 mm, L=9.53 mm, T=3.2 mm, R=12.7 mm, W=3.14 mm, H=9.53 mm.

Compression Testing—Compression testing was carried out according to the ASTM D 695-96 standard. This protocol recommended using a cylindrical specimen with a length twice its diameter. Cylindrical samples were fabricated of size 6 mm diameter and 12 mm length for use in this study. Five specimens of each composition were subjected to this test using the same Instron as for the above tensile tests. After removing surface aberrations using fine sandpaper, the samples were placed between the faces of a compression platen on the top and a compression anvil on the bottom (Instron, cat. no. 2501-107 for the upper platen, 2501-085 for the lower anvil). Compression was carried out to between 7% and 20% strains at a rate of 0.5 mm/min. In most cases the specimen was unloaded in a controlled manner and the hysteresis recorded. Uniform deformation was assumed. The initial cross-sectional area was used in the following calculations. The compressive strength was defined as the point at which lines from the initial linear region and terminal linear region intersected. The elastic modulus was obtained as in the tensile test.

TABLE 5

Mechanical Property Data for Tensile and Compression Tests

| Composition | | | | | | |
|---|---|---|---|---|---|---|
| NaCl (%) | TCP (%) | L-PLGA (%) | Tensile Strength | Young's Modulus | Compressive | Elastic Modulus |
| 25 | 25 | 50 | 5.7 ± 1.0 | 200 ± 57 | 13.5 ± 0.3 | 233 ± 26 |
| 35 | 15 | 50 | 5.5 ± 0.8 | 233 ± 27 | 13.7 ± 0.8 | 450 ± 79 |
| 35 | 21.7 | 43.3 | 3.3 ± 0.4 | 180 ± 14 | 6.5 ± 0.2 | 184 ± 12 |
| 40 | 15 | 45 | 4.0 ± 0.5 | 183 ± 35 | 7.0 ± 0.9 | 180 ± 50 |
| 55 | 11.25 | 33.75 | 1.6 ± 0.2 | 83 ± 18 | 2.5 ± 0.1 | 54 ± 17 |
| Literature Values | | | | | | |
| Poly(DL-lactide-co-caprolactone)(85:15)[6] | | | 1.6 | 160 | — | — |
| Poly(DL-lactide-co-glycolide)(50:50)[7] | | | 41–55 | 1,380–2,760 | — | — |
| Poly(L-lactic acid) 100,000 MW[8] | | | 50 | 2,700 | — | — |
| Cancellous Human Bone (fresh)[9] | | | ~8 | 700–1,000 | 10–20 | — |
| Cortical Human Bone (fresh)[9] | | | ~100 | ~15,000 | ~150 | — |

* n = 3 or 4

A set of samples in which the composition of L-PLGA (85:15), salt, and TCP were systematically varied was tested. A summary of the tensile strength, compressive strength, and derived values of the elastic modulus is presented in Table 5; each point represents the mean of 3–4 different specimens. The tensile strength and Young's modulus are also given for several reference materials in Table 5. The tensile data for 25% NaCl, 25% TCP, 50% L-PLGA was difficult to estimate due to slippage in the grips, resulting in excessive strains. Note that the listed values are of comparable magnitude to those obtained from the literature for poly(DL-lactide-co-caprolactone) (85:15) 130,000 MW and poly(L-lactic acid).

The following general observations were made: (1) increasing porosity decreased the elastic modulus, tensile strength, and yield strength; (2) increasing polymer content increased the strength and elastic moduli; (3) specimens with a higher fraction of TCP tended to exhibit brittle fracture under tension while samples with a lower fraction of TCP displayed ductile rupture; and (4) increasing the TCP content decreased the percent elongation to failure.

The data show some expected trends. Both the tensile and compressive strengths decrease as the void fraction in the device increases from 25% to 55%. Likewise, except for one anomalous result, the Young's modulus and elastic modulus decrease with increasing void fraction. Under ideal conditions, one expects values of the Young's modulus (obtained by tensile testing) to correspond exactly to the values of the elastic modulus obtained by compression testing. Often, values obtained by compression testing are slightly higher due to friction from the plates. In the samples tested here, it is striking that such agreement was obtained (with the exception of the 35% NaCl: 15% TCP:50% PLGA specimen) between the two different methods. This is especially significant because the orientation of the devices during fabrication was not the same in the samples used for each test. Tensile testing was carried out with samples built so that layers are aligned with the direction of strain, while the compression samples were built so that the layers were aligned normal to the direction of strain.

Values for pure, dense L-PLGA (85:15) 242,000 MW polymer are not available, but are expected to be comparable to those of PLA/PCL (85:15) 200,000 MW. The strength and elastic modulus parameters for all the porous devices exceed those reported for this reference polymer. Values for the tensile and compressive strengths of these devices are comparable to those of cancellous bone. This suggests that these devices have acceptable mechanical properties for in vivo applications.

EXAMPLE 7

Polymeric Components with Channel Architecture

The development of devices designed specifically to encourage cartilage regeneration, proceeded with two main considerations: materials selection and macroscopic architecture. The materials composition was selected to yield a high porosity and to degrade within several weeks. Two primary polymer combinations involving PLGA and PLA were evaluated for their use in cartilage devices. Two variants of macroscopic staggered channel architectures were developed. The objective of the macroscopic channels was to facilitate cell seeding and proliferation. The desired macroscopic channel size was chosen to be approximately 200 µm to maximize the surface area available for cell seeding without compromising structural integrity or homogeneous tissue formation.

Cartilage Batch A

This batch of cartilage devices, referred to as Batch A, included a 1:1 ratio of D,L-PLGA (50:50) 50,000 MW (Boehringer Ingelheim) with free acidic side chains to L-PLA 27,000 MW (Birmingham Polymers). The polymer particle size was 63–106 µm. PLGA with free acidic side chains was chosen to increase the rate of degradation of the device since previous results with standard PLGA suggested that faster degradation may be desirable. A 90 wt % NaCl and 10% PLA-PLGA mixture was used to obtain high porosity. The pore sizes were expected to be larger than the NaCl particle size, which was 106–150 µm. After leaching on an orbital shaker at 37° C. for 48 hours, these devices shrank 8.3% in diameter and 20% in thickness. The disks were fully leached after 7 hours, according to the silver nitrate assay, with a 90% weight loss (i.e., porosity). No residual chloroform was detected in these disks (n=5).

Batch A contained staggered channels that did not fully go through the thickness of the device, as shown in FIG. 4f. This was to model the cartilage-bone composite device in which the bone region will not contain macroscopic channels. The macroscopic staggered channel architecture was created with layers containing grooves traversing the diameter (or arc) of the disk (FIGS. 4a–d). The bottom layer contained no macroscopic channels (FIG. 4e). Grooves were formed by not depositing chloroform on sections 0.675 mm in width within the layer. The grooves were spaced 2.05 mm apart. Sixteen holes were constructed on the top face of the device superposed over the grooves. These holes were formed by printing a layer of grooves, rotating the print bed 90°, and printing another set of grooves without spreading additional powder. This effectively double-printed a significant portion of device matrix with chloroform. Double-printing may also improve mechanical properties of the final device by more completely dissolving the polymer and thus create a stronger bond between the polymer particles. The channel size was observed to be 182±37 µm in the actual devices. The drawback of this architecture design is that the two sets of grooves lie parallel to each other, potentially causing a structural weakness. This was not a critical concern if the devices are to be seeded statically.

The scanning electron micrograph (Evans East, Plainsboro, N.J.) of the cross-section shows evidence of the staggered channel. Some of the features were lost upon sectioning the device. The SEM of the surface also reveals the porous network, which includes primary pores that were greater than 100 microns and secondary pores less than 10 microns in size.

Cartilage Batch B

Cartilage devices, referred to as Batch B, were fabricated as a stand-alone cartilage replacement product. The devices needed sufficient strength to withstand the fluid flow during culture conditions in a bioreactor. Batch B was similar to Batch A but some improvements were made in the materials composition and the macroscopic architecture to satisfy these performance requirements. To minimize the pressure build up from fluid flow, macroscopic channels running completely through the device were used, as shown in FIG. 5f. In addition, supporting walls were used in the layers containing long grooves (FIGS. 5b and d), and these grooved layers were offset 90° from each other. Channels are shown in FIGS. 5a, c, and e. The materials and architecture of these devices were the same as those used in the cartilage region of the cartilage-bone composites. FIG. 5f shows a schematic cross-section of a Batch B device. The macroscopic channels are the dark regions outlined in the upper corners.

Salt Leaching

After leaching for 48 hours, the devices shrank 5.3% in diameter and 7% in thickness. After leaching for 7 hours, the devices were fully leached according to the silver nitrate assay. These devices were estimated to be 90% porous based on the weight change from leaching which is an agreement with the design planned. Residual chloroform analysis, which has a lower detection limit of ~50 ppm, suggests a negligible amount of chloroform was present (n=4).

Differential Scanning Calorimetry

Differential scanning calorimetry was performed on batches fabricated of devices contain a 1:1 ratio of D,L-PLGA and L-PLA. Since D,L-PLGA is amorphous and L-PLA is crystalline, these devices had both glass transition temperatures and melting temperatures. All batches had a glass transition temperature of 53° C. and melting temperature of 161° C. (n=3) demonstrate consistent physical properties between fabrication runs.

EXAMPLE 8

Composite Device for Cartilage and Bone Regeneration

Devices having structures consisting of an upper cartilage component, a transition zone, and a lower bone component for insertion and anchoring into the underlying bone of osteochondral defects, were made. The materials used in the bone portion of the cartilage-bone composite are a slow degrading PLGA, tri-calcium phosphate (CaP), and NaCl. The NaCl was leached out to form micropores in the final device.

A trial batch of cartilage-bone composite devices was fabricated with a bone region, a transition region, and a cartilage region with macroscopic channels identical to that of Cartilage Batch A. The overall dimensions of the product were 8 mm×1 cm before drying and salt leaching. The objective of this development batch was to evaluate the lamination and mechanical integrity of the final device.

Cartilage-Bone Composite Design Description

Sixteen staggered channels were incorporated into the microarchitecture of these devices. The channels were a nominal 0.675 mm square and were spaced 2.05 mm. Two layers of channels were separated by three layers of walls, 1.375 mm wide and spaced 2.05 mm. A detachable print plate was used to allow rotation of the powder bed underneath the stencil. Each channel layer included printing on the non-rotated and the rotated powder bed. A manual roller was used to spread powder.

Five different polymer combinations were used in the powder bed to produce cartilage-bone disks. The sequence was as follows: 3 layers of stilts, 22 layers of bone region, 6 layers of transition region, and 10 layers of cartilage region using staggered channels (Table 6). Double-sided tape was applied and stilts were constructed of three layers 200 µm each. Stilts were printed in a crosshair configuration, with two adjacent lines per leg. The polymer combination for region 1 made up the stilts and the bone portion of the device (layers 1 to 22). A 1-cm cloverleaf stencil was used for the bone and first two transition regions. Powder combinations for regions 2, 3, and 4 with every two layers of powder spread. The powder combination for region 5 made up the cartilage portion of the device, which included 10 layers of channel architecture. The architecture for region 5 used the design shown in FIG. 5 and as described for Cartilage Batch B in Example 6. Construction of channels required printing on a layer then rotating the plate 90° and then printing again on the same layer (in a specific pattern). The top right corner of the plate was registered to the walls of the piston housing. The 16 channels arranged in a 4×4 array, were nominally 0.675 mm square and were spaced 2.05 mm apart. Two layers of channels were separated by two layers of transition channels. The transition channels were similar to normal channels, but were nominally 0.675 mm wide and 1.90 mm long.

The resulting cartilage-bone composite devices included a unique macroscopic architecture in addition to the gradients of materials. The bottom of the device was approximately 5 mm thick and was fabricated with a cloverleaf stencil for enhanced bone ingrowth. The next six layers included the transition region with the bottom four layers using the cloverleaf stencil. The top two layers of the transition region used the disk stencil to avoid mechanical strength concerns. The top 2 mm of the composite, the cartilage region, was fabricated with macroscopic staggered channel architecture. Minor modifications were made to enhance the structural integrity of the device. For increased support, thin walls were added in the long grooves. The grooves were also rotated 90° with respect to each other.

The fabrication parameters, machine settings, and materials producing the best results for the bone-composite device are shown below.

Printin Parameters: flow rate: 1.2 ml/min reservoir P: 18 psig print speed: 125 cm/s line spacing: 125 µm Materials:

Binder=Solvent: 100% chloroform (Fisher Scientific)

TABLE 6

Powder bed constituents by region and layers

| Region | Layers, 200 μm @ | Powder Components | Percent by Weight in Powder Bed | Particle Size | Stencil (Shape) |
|---|---|---|---|---|---|
| Stilt | −3 layers | Same as below | | | |
| 1 - Bone | 1–22 | NaCl | 55.0% | 125–150 μm | 1 cm cloverleaf |
| | | L-PLGA (85:15) 242,000 M.W | 33.8% | 38–150 μm | |
| | | Tricalcium Phosphate | 11.2% | 38–106 μm | |
| 2 - Transition | 23–24 | NaCl | 65% | 106–150 μm | 1 cm cloverleaf |
| | | L-PLGA (85:15) 242,000 M.W | 30.0% | 38–150 μm | |
| | | L-PLA 27,000 M.W. | 2.5% | 63–106 μm | |
| | | D, L-PLGA (50:50) 50,000 M.W | 2.5% | 63–106 μm | |
| 3 - Transition | 25–26 | NaCl | 75.0% | 106–150 μm | 1 cm cloverleaf |
| | | L-PLGA (85:15) 242,000 M.W | 15.0% | 38–150 μm | |
| | | L-PLA 27,000 M.W. | 5.0% | 63–106 μm | |
| | | D, L-PLGA (50:50) 50,000 M.W | 5.0% | 63–106 μm | |
| 4- Transition | 27–28 | NaCl | 85.0% | 106–150 μm | 1 cm round disk |
| | | L-PLGA (85:15) 242,000 M.W | 5.0% | 38–150 μm | |
| | | L-PLA 27,000 M.W. | 5.0% | 63–106 μm | |
| | | D, L-PLGA (50:50) 50,000 M.W | 5.0% | 63–106 μm | |
| 5 - Cartilage | 29–38 | NaCl | 90.0% | 106–150 μm | 1 cm round disk |
| | | L-PLA 27,000 M.W. | 5.0% | 63–106 μm | |
| | | D, L-PLGA (50:50) 50,000 M.W | 5.0% | 63–106 μm | |

Several different material compositions were incorporated into the composite device structure to form the bone, transition, and cartilage regions. The materials were chosen to minimize the detrimental effects of shrinkage. Variables that were fixed were 90% NaCl content for the cartilage region and leaching temperature (temperature used for cell culture).

Finishing

The large size of the composites (8 mm in height) necessitated leaching for periods much longer than previous disk devices. It was discovered that during exposure to prolonged leaching (>24 hours), the cartilage region delaminated between the cartilage and transition regions when the cartilage region was composed of D,L-PLGA without acidic side-chains. The cause of the delamination was attributed to a significant level of differential shrinkage between these two regions. The adjacent transition region was found to only shrink 3.8% in diameter compared to the 8.3% of the cartilage region. This caused excessive shear stress and eventually resulted in delamination. This level of shrinkage was not encountered before, and changes in either the leaching process or device composition may have contributed to the delamination.

A study was performed to investigate the parameters suspected to cause shrinkage and to improve the structural integrity of the composite devices. The approach was to either reduce the amount of cartilage region shrinkage or encourage more shrinkage of the transition region. The results of the study are listed below.

1. Removing residual solvent with liquid $CO_2$ significantly reduced shrinkage.
2. Shrinkage increased with increasing leaching time.
3. Leaching at room temperature reduced shrinkage compared to leaching at 37° C.
4. Shrinkage occurred during the leaching phase and not afterwards during drying.
5. The use of PLGA(50:50) with free acidic side chains increased shrinkage versus regular PLGA(50:50)
6. Devices containing 90% NaCl shrank more than those with 85% NaCl.
7. Macroscopic channels did not significantly affect shrinkage.
8. The layer thickness used in fabrication did not influence shrinkage.
9. Double-printing (versus single-printing) did not affect shrinkage.
10. Devices composed of crystalline L-PLA 141,000 MW and 75% or 90% NaCl shrank less than 2%.

It has been reported that L-PLA has a glass transition temperature of 57–65° C., and D,L-PLGA (50:50) undergoes a glass transition near 45–55° C. Devices made with a 1:1 ratio of D,L-PLGA(50:50) 50,000 and L-PLA 27,000 have a glass transition temperature of approximately 53° C. Thus, it is unlikely that the shrinkage occurred due to plastic flow of the amorphous polymer while leaching at 37° C. These results suggest two possibilities. The polymer in the device contains residual elastic strain around the NaCl particles. When this supporting NaCl is leached out, the polymer may partially collapse, resulting in shrinkage of the overall dimensions of the device possibly due to the hydrostatic pressure to which the devices are subjected during the leaching process.

Therefore, the most favorable candidate for cartilage device fabrication as determined by the shrinkage study was the use of PLGA without acidic side chains and $CO_2$ drying before leaching. A 1:1 ratio of D,L-PLGA (50:50) 50,000

MW and L-PLA 27,000 MW was used for the cartilage region. The transition region included a gradient of NaCl from 85% to 65%, of 1:1 PLGA:PLA from 10% to 5%, and a gradient of L-PLGA (85:15) 242,000 MW from 5% to 30%, from the cartilage region to the bone region. The bone region was fabricated with 55% NaCl and a 3:1 ratio of PLGA (85:15) to TCP. This was chosen as the presumed optimal composition for osteoconduction and mechanical strength. The composite devices were incubated in 37° C. static PBS solution for a period of one month to verify mechanical integrity. No delamination or other defects were observed.

Performance of the device design. Macroscopic staggered channels in the cartilage portion of the device allow chondrocytes to be seeded in vitro throughout the thickness of the device, not just on one surface. This is important for cartilage formation since chondrocytes cannot migrate easily over distances larger than about 2 mm. Thus, the staggered channel design facilitates chondrocyte seeding directly into the center of the cartilage portion of the device. More homogeneous seeding promotes faster homogeneous cartilage formation. In association, the staggered channels facilitate the transport of nutrients to the cells and removal of cellular by-products and polymer degradation by-products away from the cells during culture in cell growth media. The bone implantable portion of the device does not have staggered channels for two reasons: osteocytes are highly migratory and therefore do not need such a configuration and to impart mechanical strength to this portion of the device. The latter property is an important characteristic enabling the device to withstand the forces of surgical implantation.

EXAMPLE 9

Scaffolds for Use as Tissue Engineered Substitutes

In vitro tissue formation by numerous cell types was tested on biodegradable or biostable synthetic scaffolds to engineer dermis, cartilage or smooth muscle for human transplantation. Scaffolds differed by their chemistry, structure (e.g., dimensions, architecture, pore size, or void fraction [VF]) and fabrication (e.g., woven, knitted, felted, braided, solvent cast as sponges, or 3-D printed as described above. Materials included nylon, poly(glycolic acid), poly (ethylene terephthalate), poly($\epsilon$-caprolactone), poly-L-lactic acid or poly(D,L-lactide co-glycolide)/poly(L-lactic acid). Human- or animal-derived cells (dermal and arterial fibroblasts, keratinocytes, articular chondrocytes, arterial smooth muscle cells and arterial endothelial cells) were cultured on scaffolds statically or dynamically for up to eight weeks. Analyses were customized per engineered tissue (quantitative MTT and DNA tests for metabolic activity and cell number, respectively; DMMB assay for glycosaminoglycans, Sirius Red assay for collagen, image analyses for pre- and post-culture dimensions, scaffold and tissue mechanics, and qualitative immunostaining and histology).

Figure 6A:
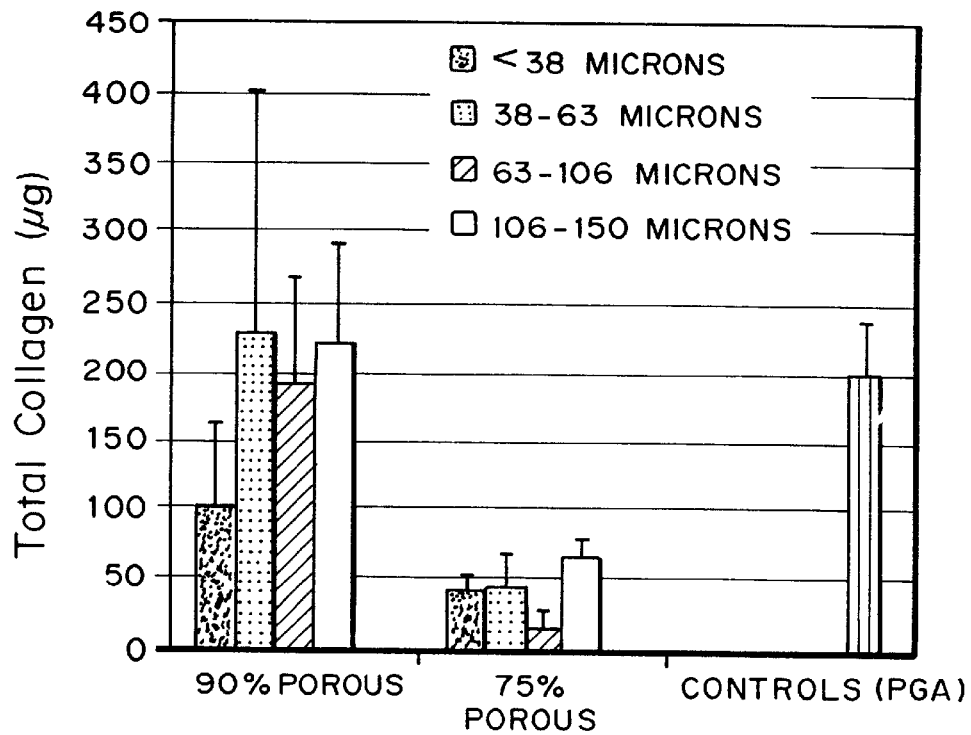
FIG. 6a is a graph of the total collagen (micrograms) as a function of the porosity, either 90% or 75%, of the scaffold, at one of four pore sizes, less than 38, 38–63, 63–106, and 106–150 microns.
Figure 6B:
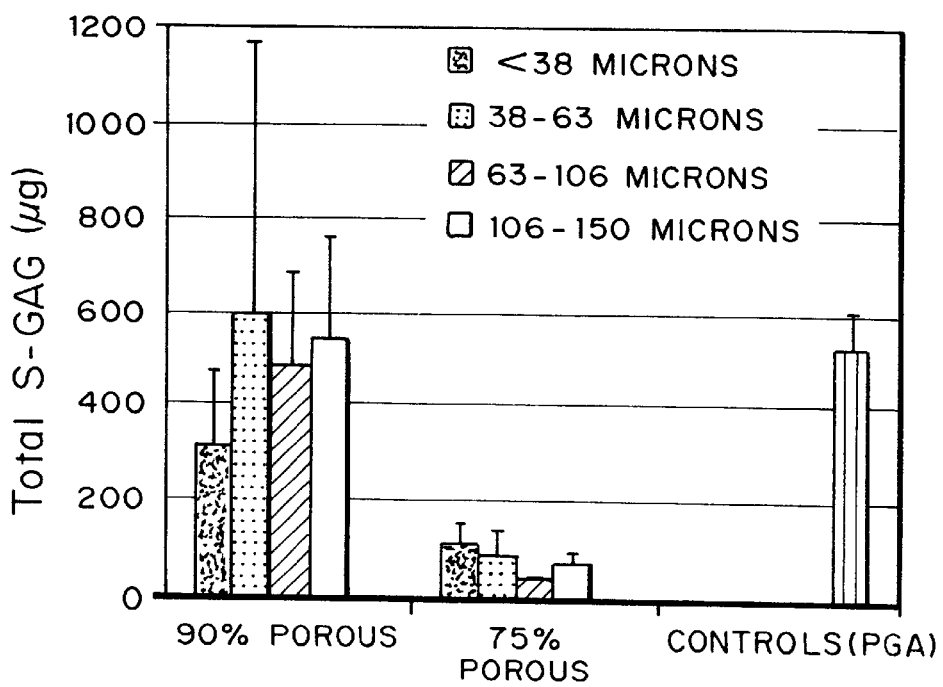
FIG. 6b is a graph of total sulfated glycosaminoglycan (micrograms) as a function of the porosity, either 90% or 75%, of the scaffold, at one of four pore sizes, less than 38, 38–63, 63–106, and 106–150 microns.

The data showed that human and animal cell types adhered to, proliferated and readily produced tissue within scaffolds of various chemistries. However, the ingrowth, distribution, orientation, and viability of cells and the gross morphology of constructs were influenced by both cell type and scaffold features (pore size, VF, fiber density, degradation). The depth and uniformity of colonization and amount of extracellular matrix formed by chondrocytes, fibroblasts, smooth muscle cells and endothelial cells corresponded to the pore size in 3DP scaffolds, as shown in FIGS. 6a and 6b discussed in more detail in Example 10. In particular, pore sizes of less than 38 microns did not promote cell attachment and growth, and the best growth and proliferation was obtained with porosities of 90% as compared to 75%. Fibroblast orientation in felts and braids followed the random or linear polymer fiber arrangement, respectively. Fibroblasts on nylon meshes formed monolayers or 3-D tissue depending on the particle sieve size. These results show that by prescribing scaffold features, one can regulate the cellular destination, orientation and extracellular matrix production on scaffolds in vitro to consistently form viable, confluent tissues for transplantation.

EXAMPLE 10

Tissue Engineered Cartilage Constructs

Articular cartilage defects have a limited ability to heal. Tissue engineered constructs made by growing cells on highly porous PGA scaffolds have been used to repair osteochondral lesions. The macroscopic architecture of scaffolds used in tissue engineering can have a dramatic affect on the cellular incorporation and matrix deposition. This study was designed to examine the effect of scaffold porosity and pore size on chondrocyte attachment, growth, and formation or deposition of a cartilage specific extracellular matrix.

Materials and Methods: PLLA scaffolds of varying porosity and pore size were fabricated using the three-dimensional printing process described above. The macroporous structure in the scaffolds was created by incorporation of a porogen, NaCl, followed by leaching of NaCl from the scaffolds. The porosity of the scaffolds was controlled by altering the weight ratio of polymer to NaCl particles incorporated into the scaffold. Eight batches of PLLA scaffolds were manufactured. Of the eight batches, four were made with a salt fraction of 75% and four were made with a 90% salt fraction, resulting in scaffolds having an approximate porosity of 75% and 90% porosity, respectively. In addition, scaffold pore size was controlled by using NaCl of specified particle sizes in the fabrication process. The NaCl particles used in the scaffold fabrication were sieved into sizes <38, 38–63, 63–106, and 106–150 microns to create scaffolds with pore sizes defined by these particle sizes. One batch of scaffolds was made at each pore size range for each of the two porosities. Scaffolds were 10 mm in diameter and 2 mm thick. PGA entangled meshes were used as control scaffolds and have an approximate porosity of 97% and fiber spacing of 90 microns. All scaffolds were seeded on one side with 4e6 primary ovine articular chondrocytes (OAC) from juvenile sheep via a bidirectional syringe method and cultured for 4 weeks in a bioreactor system. Cell-seeded constructs were harvested post-seed for functional cell distribution by MTT and total cell number by DNA analysis. Constructs harvested after 4 weeks of culture were analyzed for MTT staining as well as DNA, sulfated glycosaminoglycan (S-GAG), and collagen content.

Results: The results are shown in FIGS. 6a and 6b. Chondrocytes were found to attach, grow, and deposit hyaline-like matrix in all scaffolds studied. The 90% porous scaffolds supported more uniform cell seeding than the 75% porous scaffolds, for all pore sizes, as demonstrated by MTT stained samples. By four weeks in culture, the cells had proliferated to over 5 fold of their original numbers in the 90% porous scaffolds and to a lesser extent in the 75% porous scaffolds. Greater amounts ($p<0.01$) of sulfated-GAG (FIG. 6b) and collagen (FIG. 6a) were found in the 90% scaffolds compared to the 75% porous scaffolds. Similar amounts of S-GAG and collagen were found in the 90% 3DP scaffolds as the PGA control scaffolds (FIGS. 6a and 6b). Examination of histological samples also confirmed that more cartilaginous matrix was produced in the 90% porous scaffolds. Pore size of the scaffolds did not have a significant effect on any of the quantitative measurements (DNA, S-GAG, and collagen) for both porosities. Nevertheless, scaffolds of both porosities allowed for more homogeneous cell seeding and uniformly distributed matrix with increasing pore size.

The results demonstrate that tissue engineered constructs may be modified by controlling the scaffold architecture. 3DP scaffolds composed of 90% porous PLLA contained equivalent cartilage matrix levels as compared to PGA scaffolds. In contrast, chondrocytes deposited much less (p<0.05) hyaline-like matrix in the 75% porous TheriForm scaffolds. More uniform cell seeding and deposition of safranin-O stained matrix was found in the scaffolds of greater pore sizes. This study demonstrates that scaffolds of various porosity and pore size can have a dramatic effect on the extent and uniformity of cell seeding and matrix deposition, establishing that these two parameters can be altered in order to either promote or limit the incorporation of cells or ingrowth of tissue.

We claim:

1. A porous device for tissue engineering formed by solid free form fabrication comprising
    a first region having a first pore size, porosity, macroarchitecture, microarchitecture, and composition selected to promote attachment, proliferation, and/or differentiation of a first cell type; and
    a second region seamlessly joined to the first region by a transition zone, wherein the second region has a second pore size, porosity, macroarchitecture, microarchitecture, and/or composition selected to (i) promote attachment, proliferation, and/or differentiation of a second cell type, or (ii) limit attachment or proliferation of either the first or second cell type,
    wherein the transition zone has gradients of pore size, porosity, macroarchitecture, microarchitecture, and/or composition effective to avoid delanination of the first or second regions.

2. The device of claim 1 wherein the transition zone comprises a gradient of pore sizes, porosities, and/or compositions between and seamlessly joining the first region and the second region.

3. The device of claim 1 wherein the first region and second region are fabricated from a polymeric material in the form of a powder using three dimensional printing.

4. The device of claim 1 wherein the porosity in at least one region is greater than about 90%.

5. The device of claim 1 wherein at least one region or a gradient within a region comprises osteogenic, osteoinductive, and/or osteoconductive materials.

6. The device of claim 1 further comprising a bioactive agent, diagnostic agent, or non-polymeric particles enhancing cell attachment or providing structural properties.

7. The device of claim 6 wherein the bioactive agent enhances differentiation, proliferation, and/or attachment of cells or specific cell types.

8. The device of claim 1 further comprising particles of leachable salt having a defined diameter dispersed in at least one region.

9. A method of making a porous device for tissue engineering comprising at least two regions, the method comprising
    (a) making, by solid free form fabrication of a material, a first region having a pore size, porosity, macroarchitecture, microarchitecture, and composition selected to promote attachment, proliferation, and/or differentiation of a first cell type,
    (b) making, by solid free form fabrication of a material, a transition zone next to the first region; and
    (c) making next to the transition zone, by solid free form fabrication of a material, a second region having a pore size, porosity, macroarchitecture, microarchitecture, and/or composition selected to (i) promote attachment proliferation, and/or differentiation of a second cell type, or (ii) limit attachment or proliferation of either the first or second cell type,
    wherein the transition zone has gradients of pore size, porosity, macroarchitecture, microarchitecture, and/or composition effective to avoid delamination of the first or send regions.

10. The method of claim 9 wherein the transition zone comprises a gradient of pore sizes, porosities, and/or compositions between and seamlessly joining the first region and the second region.

11. The method of claim 9 wherein the solid free form fabrication is three dimensional printing.

12. The method of claim 9 wherein the material forming the first region, the second region, or both comprises a polymeric material.

13. The method of claim 9 wherein the forming in (a) and/or (b) comprises incorporating a coacervate of non-polymeric particles coated with polymer.

14. The device of claim 1 wherein at least one of the region has a cross-sectional design substantially in a form selected from the group consisting of tubes, coils, clovers, inverted clovers, honeycombs, and slots.

15. The device of claim 1 wherein the microarchitecture of at least one region promotes the incorporation of cells and/or ingrowth of tissue.

16. The device of claim 1 wherein the microarchitecture of at least one region limits the incorporation of cells and/or ingrowth of tissue.

17. The device of claim 1 wherein the surfaces of at least one region are modified by surfactants, cell attachment peptides, or bioactive agents.

18. The device of claim 2 wherein at least one region, the transition zone, or both, comprise layers of mixtures of two or more materials, wherein the layers together provide within the at least one region, transition zone, or both, gradients of two or more of the materials.

19. The device of claim 18 wherein one of the materials is leachable and another of the materials is non-leachable.

20. The device of claim 19 wherein the leachable material is sodium chloride.

21. The device of claim 18 wherein the mixtures further comprise inorganic particles.

22. The device of claim 21 wherein the inorganic particles are selected from the group consisting of bone, tricalcium phosphate, hydroxyapatite, and combinations thereof.

23. The device of claim 1 wherein the polymeric material comprises a polymer selected from the group consisting of poly(alpha)esters, poly($\epsilon$-caprolactone)s, polyanhydrides, polyarylates, polyphosphazenes, polyhydroxyalkanoates, and polysaccharides.

24. The device of claim 23 wherein the polymer is poly(lactic acid-co-glycolic acid) or poly(lactic acid).

25. The device of claim 24 wherein the poly(lactic acid-co-glycolic acid) has free acidic side chains to increase the rate of degradation of the polymer.

26. The device of claim 1 wherein the polymeric material is formed from coacervated particles.

27. The device of claim 26 wherein the coacervated particles are non-polymeric particles coated with a polymer.

28. The device of claim 27 wherein the non-polymeric particles are selected from the group consisting of bone particles, hydroxyapatite particles, and calcium phosphate particles.

29. The device of claim 27 wherein particles are coated with a poly(lactic acid-co-glycolic acid).

30. The device of claim 1 wherein the first region is a bone regeneration region and the second region is a cartilage regeneration region.

31. The device of claim 30 wherein the porosity of the cartilage region is about 90% or more and the pore size of the cartilage region is 38 $\mu$m or more.

32. The device of claim 31 wherein the pore size of the cartilage region is between about 106 and 150 $\mu$m.

33. The device of claim 30 wherein the porosity of the bone region is between about 35 and 55%, and the pore size is between about 125 and 150 $\mu$m.

34. The device of claim 30 wherein the bone region has a clover shape.

35. The device of claim 30 wherein the bone region has a honeycomb or hollow cylinder shape.

36. The device of claim 30 wherein the bone region comprises a 3:1 ratio of poly(lactic acid-co-glycolic acid) to tricalcium phosphate or hydroxyapatite.

37. The device of claim 36 wherein the bone region further comprises 55% salt.

38. The device of claim 30 wherein the cartilage region comprises a 1:1 ratio of poly(lactic acid-co-glycolic acid) and poly(lactic acid).

39. The device of claim 38 wherein the cartilage region comprises 90% salt.

40. The device of claim 30 further comprising a transition region between the first region and the second region.

41. The device of claim 40 wherein the transition region includes a gradient of a salt from 85% to 65%, a gradient of 1:1 poly(lactic acid-co-glycolic acid) (50:50):poly(lactic acid) from 10% to 5%, and a gradient of poly(lactic acid-co-glycolic acid) (85:15) from 5% to 30%, from the cartilage region to the bone region.

42. The device of claim 2 wherein one or more of the regions and transition zone further comprise one or more macroscopic channels suitable for cell seeding and proliferation.

43. The device of claim 42 having two or more layers of channels, wherein the channels of one layer are in a staggered orientation, an offset orientation, or both, with respect to the channels of adjacent layers.

44. The device of claim 43 wherein the channels in the layers form flow paths that extend completely through the device.

45. The device of claim 43 wherein the channels in the layers form flow paths that do not extend completely through the device.

46. The device of claim 43 wherein the channels are offset about 90° with respect an axis perpendicular to the layers.

47. The device of claim 1 wherein cells are selectively excluded in vitro from one or more regions of the device by means of the pore size and/or porosity of said one or more regions.

48. The device of claim 47 wherein cells proliferate in vivo in said one or more regions.

49. The device of claim 1 wherein at least one region is treated with a substance to prevent cell attachment in vitro, but in which cells will grow into in vivo.

50. The device of claim 1 wherein the first region is a suitable for weight bearing loads and the second region is a suitable for soft tissue regeneration.

51. A device for regeneration of cartilage comprising
a porous matrix formed by three dimensional printing of a polymer,
wherein the matrix contain staggered channels and has a porosity of 90% or more.

52. The device of claim 51 wherein the matrix comprises primary pores having a size greater than 100 $\mu$m and secondary pores having a size less than 10 $\mu$m.

53. The device of claim 50 further comprising chondrocytes seeded within the channels.

54. The method of claim 13 further comprising leaching the leachable particles from the device.

55. The method of claim 54 wherein residual solvent is removed from the device using liquid or supercritical carbon dioxide prior to the leaching.

56. The method of claim 9 wherein the polymeric material in step (a) and/or step (b) is a coacervate of non-polymeric particles coated with polymer.

57. The method of claim 9 further comprising seeding one or more regions of the device with cells.

58. The method of claim 9 wherein the device has at least two regions, one of which is a bone regeneration region and one of which is a cartilage regeneration region.

59. The method of claim 58 further comprising selectively seeding the cartilage region with cells in vitro, while simultaneously excluding cell attachment in the bone region.

60. The method of claim 59 wherein the selective seeding is achieved as a function of the relative porosity of the two regions.

61. The method of claim 57 wherein the cells are chondrocytes.

62. The method of claim 9 wherein the solid free form fabrication method is selected from stereo-lithography, selective laser sintering, ballistic particle manufacturing, and fusion deposition modeling.

* * * * *